(12) United States Patent
Mannesse et al.

(10) Patent No.: US 8,071,532 B2
(45) Date of Patent: Dec. 6, 2011

(54) USE OF C1 INHIBITOR FOR THE PREVENTION OF ISCHEMIA-REPERFUSION INJURY

(75) Inventors: Maurice Mannesse, Leiden (NL); Johannes Henricus Nuijens, Heiloo (NL); Frank Pieper, Heemstede (NL); Maria Grazia De Simoni, Milaan (IT); Gijsbertus Johannes Ziere, Koudekerk Aan Den Rijn (NL)

(73) Assignee: Pharming Intellectual Property B.V., Leiden (NL)

( * ) Notice: Subject to any disclaimer, the term of this patent is extended or adjusted under 35 U.S.C. 154(b) by 433 days.

(21) Appl. No.: 12/158,987

(22) PCT Filed: Dec. 19, 2006

(86) PCT No.: PCT/NL2006/050321
§ 371 (c)(1),
(2), (4) Date: Jun. 23, 2008

(87) PCT Pub. No.: WO2007/073186
PCT Pub. Date: Jun. 28, 2007

(65) Prior Publication Data
US 2008/0305993 A1 Dec. 11, 2008

Related U.S. Application Data

(60) Provisional application No. 60/760,944, filed on Jan. 23, 2006.

(30) Foreign Application Priority Data

Dec. 21, 2005 (EP) .................................... 05112630

(51) Int. Cl.
*C07K 14/00* (2006.01)

(52) U.S. Cl. .......................................... 514/1; 530/350
(58) Field of Classification Search ....... 514/1; 530/350
See application file for complete search history.

(56) References Cited

U.S. PATENT DOCUMENTS

| 7,067,713 | B2 | 6/2006 | Nuijens et al. |
| 7,544,853 | B2 | 6/2009 | Nuijens |
| 2003/0140358 | A1 | 7/2003 | Nuijens et al. |
| 2005/0223416 | A1 | 10/2005 | Nuijens et al. |
| 2006/0142220 | A1 | 6/2006 | Berkel et al. |
| 2007/0185011 | A1 | 8/2007 | Nuijens |

FOREIGN PATENT DOCUMENTS

| WO | 0157079 A2 | 8/2001 |
| WO | 2004100982 A1 | 11/2004 |

OTHER PUBLICATIONS

C. de Zwaan, et al., "Continuous 48-h C1-inhibitor treatment, following reperfusion therapy, in patients with acute myocardial infarction", European Heart Journal 2002, vol. 23, pp. 1670-1677.
S. Friesecke, et al., "C1-Esterase-Inhibitor als Ultima-ratio-Therapie bei volumen-und katecholaminrefraktarem Schock infolge Ischamie-Reperfusionsschaden nach langer Reanimation", Intensivmed 2002, vol. 39, No. 7, pp. 610-616.
Marco Cicardi, et al., "C1 inhibitor: molecular and clinical aspects", Springer Semin Immun, Nov. 3, 2005, vol. 27, pp. 286-298.
Mirela Scherer, et al., "C1-Esterase Inhibitor Reduces Reperfusion Injury After Lung Transplantation", Ann. Thorac. Surg., 2002, vol. 73, pp. 233-239.
Claudio Storini, et al., "C1-inhibitor protects against brain ischemia-reperfusion injury via inhibition of cell recruitment and inflammation", Neurobiology of Disease, 2005, vol. 19, pp. 10-17.
Akita Nobuhisa, et al., "Protective Effect of C1 Esterase Inhibitor on Reperfusion Injury in the Rat Middle Cerebral Artery Occlusion Model", Neurosurgery, Feb. 2003, vol. 52, No. 2, pp. 395-401.
DeSimoni, et al. "The Powerful Neuroprotective Action of C1-Inhibitor on Brain Ischemia-Reperfusion Injury Does Not Require C1q". *American Journal of Pathology*, vol. 164, No. 5, pp. 1857-1863 May 2004.

*Primary Examiner* — Karen Carlson
(74) *Attorney, Agent, or Firm* — Alston and Bird LLP

(57) ABSTRACT

The present invention relates to the therapeutic and prophylactic use of C1 inhibitor for preventing, reducing and treating ischemia and reperfusion injury. The C1 inhibitor of the present invention is still therapeutically effective when administered after an ischemic period and reperfusion and therefore particularly useful for unforeseen occurrences of ischemic reperfusion such as e.g. a stroke.

22 Claims, 10 Drawing Sheets

|  | Saline | Pre | Post | 3h post | 6h post | 9h post | 18h post | 24h post |
|---|---|---|---|---|---|---|---|---|
| Striatum | +++ | ++ | + | ++ | +++ | ++ | ++ | +++ |
|  | +++ | +++ | ++ | +++ | +++ | ++ | +++ | +++ |
|  | +++ | ++ | + | ++ | ++ | +++ | +++ | +++ |
|  | +++ | +++ | +++ | +++ | +++ | ++ | +++ | ++ |
|  | +++ | +++ | ++ | +++ | ++ | ++ | ++ | +++ |
|  | +++ | ++ | ++ | ++ | +++ | +++ | +++ | +++ |
| Hippocampus | +++ | - | - | - | + | - | ++ | +++ |
|  | ++ | - | - | - | ++ | ++ | - | +++ |
|  | + | - | - | + | - | ++ | + | ++ |
|  | +++ | - | - | - | ++ | + | ++ | ++ |
|  | ++ | - | - | - | + | +++ | +++ | +++ |
|  | +++ | - | - | - | +++ | + | +++ | + |
| Cortex | +++ | - | - | - | - | - | + | +++ |
|  | ++ | - | - | - | - | - | + | ++ |
|  | +++ | - | - | - | - | - | - | ++ |
|  | ++ | - | - | - | - | - | +++ | +++ |
|  | ++ | - | - | - | - | + | - | + |
|  | +++ | - | - | - | + | - | ++ | +++ |

Fig 16

| | | | Wieslab complement assay | | | |
|---|---|---|---|---|---|---|
| | | | \% Complement Activation | | | |
| | | | Classical Pathway | | MBL Pathway | |
| | | | Mean | SD | Mean | SD |
| | | PC | 100 | 7 | 100 | 16 |
| Seum sample 1 | pdC1INH | 0 umol | 111 | 2 | 103 | 10 |
| | | 15 umol | 103 | 3 | 78 | 6 |
| | | 30 umol | 99 | 3 | 61 | 6 |
| | | 75 umol | 84 | 2 | 26 | 3 |
| | rhC1inh | 0 umol | 111 | 2 | 103 | 10 |
| | | 15 umol | 106 | 4 | 59 | 4 |
| | | 30 umol | 101 | 3 | 39 | 4 |
| | | 75 umol | 74 | 2 | 12 | 1 |
| | Buffer | 0 umol | 111 | 2 | 103 | 10 |
| | | 15 umol | 113 | 6 | 97 | 6 |
| | | 30 umol | 114 | 3 | 99 | 8 |
| | | 75 umol | 112 | 2 | 98 | 9 |
| serum sample 2 | pdC1INH | 0 umol | 85 | 5 | 85 | 7 |
| | | 15 umol | 72 | 4 | 52 | 7 |
| | | 30 umol | 67 | 4 | 33 | 3 |
| | | 75 umol | 61 | 3 | 13 | 2 |
| | rhC1inh | 0 umol | 85 | 5 | 85 | 7 |
| | | 15 umol | 76 | 4 | 37 | 1 |
| | | 30 umol | 70 | 2 | 19 | 2 |
| | | 75 umol | 56 | 3 | 5 | 0 |
| | Buffer | 0 umol | 85 | 5 | 85 | 7 |
| | | 15 umol | 79 | 6 | 75 | 6 |
| | | 30 umol | 76 | 3 | 72 | 2 |
| | | 75 umol | 75 | 5 | 71 | 2 | ardiovascular disease that

USE OF C1 INHIBITOR FOR THE PREVENTION OF ISCHEMIA-REPERFUSION INJURY

FIELD OF THE INVENTION

The present invention relates to the therapeutic and prophylactic use of C1 inhibitor for preventing, reducing and treating ischemia-reperfusion injury, particularly cerebral ischemia-reperfusion injury that may occur as a result of a stroke.

BACKGROUND OF THE INVENTION

Ischemia-reperfusion injury is a well known occurring pathologic condition. It may either represent a foreseen pathologic condition or an unforeseen pathologic condition. Stroke is one of the most common types of unforeseen ischemia-reperfusion injury. Stroke is the third cause of death and the leading cause of long-term disability in industrialized countries. Stroke is a type of cardiovascular disease that affects the arteries leading to and within the brain. A stroke occurs when such arteries are blocked by a clot or bursts and results in ischemia of the cerebral tissues that are served by the blocked artery. Direct damage to the brain is caused by the interruption of the blood flow, mainly due to loss of oxygenation to the viable tissue, ultimately leading to infarction if not reversed. However if the insult is reversed (either physiologically or therapeutically) then reperfusion of the ischemic tissue may paradoxically cause further indirect damage. When there is a long duration of ischemia, the "direct" damage resulting from hypoxia alone is the predominant mechanism. For shorter duration's of ischemia, the indirect or reperfusion mediated damage becomes increasingly more important to the final outcome.

C1 inhibitor (C1INH), the inhibitor of complement C1, has been reported to display neuro-protective action by reducing ischemia-reperfusion injury in rodent models for cerebral ischemia-reperfusion. (De Simoni et al., 2003, J Cereb Blood Flow Metab. 23: 232-9; Akita et al., 2003, Neurosurgery 52: 395-400). The neuro-protective action of C1INH on brain ischemia-reperfusion injury does not require C1q (De Simoni et al., 2004, Am J. Pathol. 164: 1857-63). More recently Storini et al. (2005, Neurobiol Dis. 19: 10-7) reported that C1INH exerts an anti-inflammatory and anti-apoptotic action on ischemia-reperfusion injury through inhibition of inflammation and cell recruitment from the vasculature to the ischemic site. However, the window in time around the stroke during which administration of C1INH is therapeutically effective is rather narrow. It is therefore an object of the present invention to provide for C1INH with a broader window in terms of time of administration.

DESCRIPTION OF THE INVENTION

The present invention is based on the surprising finding that where naturally occurring plasma derived C1 inhibitor (C1INH), has lost most of its ability to reduce ischemia reperfusion injury in a mouse model for transient cerebral focal ischemia when administered after ischemia, a recombinant preparation of C1INH is still able to exert its neuroprotective effects also when injected at least 1 hour after ischemia and/or reperfusion. Surprisingly, a neuroprotective effect can still be reached when the C1INH is injected 18 hours after ischemia and/or reperfusion. The difference between the naturally occurring plasma derived C1INH and the recombinant preparation of C1INH is that the first has a plasma half life of at least 24 hours and is fully sialylated glycoprotein, and the latter has a reduced plasma half life and has a different glycosylation as compared to the plasma derived product.

A difference known between the naturally occurring plasma derived C1INH and the recombinant preparation of C1INH is the extent and type of glycosylation. The recombinant glycoprotein contains a broad array of different N-glycans, comprising oligomannose-, hybrid-, and complex-type structures, whereas the N-glycans of plasma derived C1INH are mainly composed of fully sialylated complex-type structures. As a result of the differences in glycosylation, the plasma derived glycoprotein has a plasma half life of at least 24 hours and the recombinant C1INH has a reduced plasma half life.

In one aspect the present invention therefore relates to a method for the prevention, reduction or treatment of at least one of ischemia and reperfusion injury, whereby the C1 inhibitor is administered after the ischemia and/or after the reperfusion. The method preferably comprises the step of administering an effective amount of a C1INH having a plasma half life that less than the plasma half life of a plasma derived C1INH. Alternatively, the method preferably comprises the step of administering an effective amount of a C1INH that has a different glycosylation as compared to the plasma derived C1INH. This method relates to a therapeutic and/or prophylactic use of C1 inhibitor for preventing, reducing and/or treating any type of ischemia-reperfusion injury.

A C1 inhibitor, also referred to as C1 esterase inhibitor is herein defined, as an inhibitor of complement C1. C1INH belongs to the superfamily of serine proteinase inhibitors and is the only inhibitor of C1r and C1s of the complement system and is the major inhibitor of factor XIIa and kallikrein of the contact system. In addition C1INH also inhibits other serine proteases of the coagulation and fibrinolytic systems like factor XI, tissue type plasminogen activator and plasmin (Schapira et al. 1985, Complement 2: 111; Davis, 1988, Ann. Rev. Immunol. 6: 595). Human C1INH is a protein of 500 amino acids, including a 22 amino acid signal sequence (Carter et al. 1988, Euro. J. Biochem. 173; 163). Plasma C1INH is a glycoprotein of approximately 76 kDa and is heavily glycosylated, up to 26% of its molecular mass consists of carbohydrate (Perkins et al., 1990, J. Mol. Biol. 214, 751). A C1INH for use in the methods of the present invention preferably is a protein with an amino acid sequence that has at least 65, 67, 68, 69, 70, 75, 80, 85, 90, 95, 98 or 99% identity with the amino acid sequence of the mature human C1INH as depicted in SEQ ID NO: 1.

For the purpose of the present invention, the degree of identity between two amino acid sequences refers to the percentage of amino acids that are identical between the two sequences. First, homologous polypeptide sequences are searched using the Basic Local Alignment Search Tool (BLAST) algorithm, which is described in Altschul, et al., J. Mol. Biol. 215: 403-410 (1990). Software for performing BLAST analyses is publicly available through the National Center for Biotechnology Information (www.ncbi.nlm.nih.gov/). The BLAST algorithm parameters W, B, and E determine the sensitivity and speed of the alignment. The BLAST program uses as defaults a word length (W) of 3, the BLOSUM62 scoring matrix (see Henikoff & Henikoff, Proc. Natl. Acad. Sci. USA 89: 10915 (1989)) alignments (B) of 50, expectation (E) of 10, M=5, N=−4. Next, the degree of identity (as defined above) of homologous sequences is determined using the CLUSTALW alignment algorithm (Higgins D. et al (1994). Nucleic Acids Res. 22:4673-4680) using the following parameters; Gap size: 5, Gap open: 11, Gap extension: 1, Mismatch: −15, Word size: 3.

The C1INH preferably has C1INH activity as may e.g. be assayed as described by Drouet et al. (1988, Clin Chim Acta. 174:121-30). More preferably, the C1INH is a human C1INH (hC1INH) which is understood to mean that the C1INH has an amino acid sequence that naturally occurs in man (as e.g. SEQ ID NO:1 or CAA30314) but does not mean that the C1INH is produced in and obtained from e.g. human plasma.

According to one aspect of the invention the C1INH for use in the methods of the invention preferably has a reduced plasma half life as compared to the plasma half life of plasma derived C1INH, more preferably the plasma half life of the C1INH of the invention is less than the plasma half life of C1INH derived from human plasma. By "a reduced plasma half life" is meant the negative change in circulating half life of a C1INH of the invention relative to the circulating half life of a plasma derived C1INH. In this context, a plasma derived C1INH refers to naturally occurring C1INH which is typically derived from plasma and which may be purified from plasma but is not modified in chemically or enzymatically.

Plasma half life is measured by taking blood samples at various time points after administration of the C1INH, and determining the concentration of the C1INH in each sample. Correlation of the serum concentration with time allows calculation of the plasma half life. The reduction of plasma half life of a C1INH of the invention relative to the circulating half life of a plasma derived C1INH preferably is at least about two-fold, at least about three-fold, at least about four-fold, at least about six-fold, more preferably at least about eight-fold, and most preferably at least about ten-fold. In other words, plasma half life of a C1INH of the invention preferably is less than 60, 50, 40, 30, 25, 20, 15, 12.5 or 10% of the plasma half life of a plasma derived C1INH, i.e. its naturally occurring counterpart.

E.g. the plasma half life of the C1INH of the invention that is used in the Examples herein, which is obtained from the milk of transgenic rabbits, exhibits a plasma half life in humans of about 3 hours, which about four- to eight-fold less than the average plasma half life of a plasma derived C1INH in man. It is understood that the determination of the reduction of plasma half life of a C1INH of the invention as compared to that of plasma derived C1INH is preferably performed under similar if not identical conditions, i.e. preferably at corresponding dosages, sampling regimes, in the same organism, which may be a laboratory animal such as a mouse or human subjects, and in about the same number of test subjects. Furthermore, it is understood that the average plasma half lives of both C1INH preparation are compared as may be determined by standard method of statistical analysis.

A C1INH with shorter half life, be it a naturally occurring or a recombinantly produced C1INH, may be prepared by any convenient method. It may for example be prepared in vivo in a recombinant host cell or organism that results in a C1INH with a modified carbohydrate structure (as compared to the plasma derived C1INH) or the carbohydrate structure of a naturally occurring C1INH may be chemically or enzymatically modified in vitro. Preferably, the C1INH of the invention is modified compared to the plasma derived C1INH the following way: removal of a carbohydrate moiety (from a naturally occurring variant or recombinantly expressed variant of the glycoprotein), preferably the removal of sialic acid and/or galactose from a N-linked carbohydrate chain and/or the removal of a carbohydrate chain resulting in exposure of mannose, galactose, N-acetylglucosamine and/or fucose residues.

According to another aspect of the invention the C1INH for use in the methods of the invention preferably has a different glycosylation as compared to the plasma derived C1INH. Modifications to the carbohydrate structure of a C1INH of the invention include modifications which lead to underglycosylation, overglycosylation, to the asialo form of C1INH, or any other modifications which lead to a different glycosylation pattern.

In vitro, underglycosylation may be the result of a deletion of a carbohydrate moiety or of a complete carbohydrate chain of C1INH. Modifications may involve both N- or O-linked carbohydrate chains, or only one type of chain. It may involve all the chains, or only some of the chains. Overglycosylation may for instance be the result of the addition of an extra carbohydrate moiety or a complete carbohydrate chain to the C1INH molecule. An asialo-form of C1INH or a form having a reduced level of terminal sialic acid residues may typically be obtained by removal of a sialic acid group. It is well-known that the half life of a glycoprotein in the blood is highly dependent on the composition and structure of its N- and O-linked carbohydrate groups. In general, maximal half life of a glycoprotein requires that its N- and O-linked carbohydrate groups have a terminal sialic acid. If this terminal sialic acid is not present, the glycoprotein is rapidly cleared from the blood due to the exposure of galactose residues. It is well-established that the presence of terminal galactose residues in carbohydrate moieties of glycoproteins results in enhanced plasma clearance by the asialoglycoprotein receptor in the liver. Thus in a preferred embodiment, C1INH for use in the methods of the present invention preferably has a reduced level of terminal sialic acid residues as compared to plasma derived human C1 inhibitor. Sialic acid may be removed in several ways. For instance, it may be removed chemically or enzymatically, for example, by treatment with sialidase. Suitable sialidases for this purpose are described by Chou et al. (1996, J Biol Chem. 271(32):19219-24; and 1994, J Biol Chem. 269(29):18821-6) and may e.g. be obtained from V-labs, Inc. (Covington, La., USA). In a further preferred embodiment, C1INH for use in the methods of the present invention preferably has exposed mannose, N-acetylglucosamine phosphomannose, galactose and/or N-acetylgalactosamine residues. An exposed sugar residue will usually be a terminal sugar residue on a glycan branch or at least a sugar residue that is accessible for interactions with a moiety having affinity for the residue (such as a carbohydrate binding domain). A C1INH with exposed galactose, N-acetylgalactosamine, N-acetylglucosamine, mannose, fucose or phosphomannose residues may e.g. be obtained by enzymatic treatment with one or more of β-D-N-acetylhexosaminidase, endo-β-D-galactosidase, and/or α-D-N-acetylgalactosaminidase (also obtainable form e.g. V-labs, Inc., Covington, La., USA).

In vivo, modifications of carbohydrate chains of C1INH may be introduced by using recombinant production systems. Both prokaryotic and eukaryotic cell cultures may be used, such as yeast cells, fungal cells, insect cells and mammalian cells. For example, COS cells and CHO cells are suitable mammalian production systems. Although mammalian cell culture systems have the capacity to produce glycoproteins with sialylated carbohydrate groups, optimal, natural or complete glycosylation is often difficult to achieve and consequently, recombinantly produced glycoproteins in general have a different glycosylation pattern than their natural counterparts. Usually this different glycosylation pattern is incomplete (as compared to the natural counterparts) having exposed galactose, N-acetylglucosamine and/or mannose residues. Likewise, production of C1INH in eukaryotic microorganisms like yeasts or fungi will result in C1INH with exposed mannose residues.

C1INH with modified carbohydrate structures may also be prepared in transgenic animals, preferably in non-human animals, such as in transgenic rabbits, bovine, mice, rats, goats and sheep. Preferably, such glycoproteins are expressed in the mammary glands of these non-human transgenic animals such that the glycoproteins may be obtained from the milk of the animal. The skilled person will understand that it will depend on the specific glycoprotein to be produced and on the amount which has to be produced, which transgenic animal is best used for production. A particularly preferred C1INH for use in the present invention is a C1INH that is obtained from the milk of a transgenic bovine or an animal of the order *Lagomorpha*, preferably of the family Leporidae, more preferably of the genus *Oryctolagus* and most preferably a rabbit of the species *Oryctolagus cuniculus*.

Different types of modifications to the structure of the carbohydrate chain of the C1INH protein as compared to its natural plasma-derived counterpart may be obtained from recombinant production systems, such as different glycosylation, underglycosylation or overglycosylation may be introduced separately or in combination, simultaneously or consecutively, some types may be introduced to one part of the molecule, while others are introduced to another part of the molecule. Preferred combinations of modifications contribute to the therapeutic efficacy of the protein include exposed galactose, N-acetylgalactosamine, N-acetylglucosamine, mannose, fucose and/or phosphomannose residues on the C1INH of the invention. The C1INH of the invention may e.g. have glycans of the oligomannose type or of the highmannose type. Preferably at least about 5, 10, 15, 20, 40 or 60% of the terminal residues on the glycans on the C1INH are selected from galactose, N-acetylgalactosamine, N-acetylglucoseamine, mannose, fucose and phosphomannose residues. E.g. a preferred C1INH for use in the present invention contains about 2, 4, 5, 6-fold less sialic acid as compared to its natural counterpart and/or at least about 5, 10, 15, 20, 40 or 60% of its N-linked glycans are neutral carrying terminal hexoses with equatorial 3- and 4-OH groups, such as mannose and N-acetylglucosamine. In contrast, plasma derived C1INH has no oligomannose type glycosylation. A preferred C1INH for use in the present invention e.g. is a recombinant human C1INH produced in the mammary glands of rabbits which has 5-6 fold less sialic acid as compared to its natural counterpart and about 15% of its N-linked glycans are neutral carrying terminal mannose residues.

In a preferred embodiment, the different glycosylation of the C1INH for use in the present invention results in a higher affinity for a mannose binding protein as compared to its plasma derived counterpart. The mannose binding protein (MBP) is also referred to as mannan-binding protein, mannose-binding lectin (MBL), mannan-binding lectin, or bactericidal Ra-reactive factor. MBP is a collectin that belongs to a group of soluble $Ca^{2+}$-dependent (C-type) lectins. MBP is an activator of complement via the lectin pathway (that differs from the classical and alternative pathways of complement activation). The complement system is an important component of the innate immune defense and is activated by three pathways: the classical pathway, the alternative pathway, and the recently discovered lectin or Mannose binding lectin (MBL) pathway.

The activation of the classical pathway begins when the catalytic domains C1r and C1s bind to immune complexes via the recognition protein C1q (see FIG. 11). The alternative pathway is continuously turning over at a slow rate in an antibody-independent manner and will attack particles that are not specifically protected against complement.

The lectin or MBL pathway is initiated or activated upon binding of MBL to carbohydrate structures present on various pathogens or other cellular structures. Two serine proteases: mannan-binding lectin associated serine protease (MASP)-1 and -2 (see FIG. 11) are associated with MBL and show striking similarities with the serine proteases C1s and C1r. The complex has C4- and C3-activating capacities upon binding to mannan. The complex contains two serine proteases MASP-1 and MASP-2 linked by a disulfide bond. In this form, MASP is capable of cleaving C4 and C3 resulting in their activation. The C1INH of the invention preferably has a higher affinity for a human MBP as compared to its plasma derived counterpart.

MBP recognizes exposed hexoses with equatorial 3- and 4-OH groups, such as mannose and N-acetylglucosamine and/or N-acetyl-hexosamines. A preferred C1INH of the invention therefore carries such terminal hexoses. The higher affinity for MBP, preferably human MBP of the C1INH of the invention preferably is such that it allows a more efficient targeting, binding and/or inhibition of MBP as compared to its natural plasma derived counterpart that lacks exposed mannose and N-acetylglucosamine residues. Human MBP is herein understood to refer to the protein characterized by Kawasaki et al. (1983, J. Biochem 94:937-47), having an amino acid sequence as described by Taylor et al. (1989, Biochem. J. 262 (3), 763-771; NCBI accession no. CAA34079). The structure of rat MBP complexed with an oligosaccharide is described by Weis et al. (1992, Nature. 360:127-34). For a further description of human MBP see e.g U.S. Pat. No. 6,846,649 and references cited therein.

All of these pathways (classical, alternative and lectin or MBL) generate a crucial enzymatic activity that eventually leads to the assembly of the membrane attack complex (MAC or C5b-C9) (see FIG. 11). Under physiological conditions, activation of the complement system is effectively controlled by the coordinated action of soluble and membrane-associated regulatory proteins. One of these proteins is C1 inhibitor (C1INH), a serine protease inhibitor that binds to C1s and C1r and currently the only known physiological inhibitor of the classical pathway. In addition, C1INH is able to inactivate MBL-mediated complement activation by binding and inhibiting MASP-1 and MASP-2.

The activation of the different complement pathways is preferably measured in human sera by the Wielisa kit (product no. COMPL 300, Wieslab, Sweeden). This is a commercially available enzyme immuno assay, specific for the detection of each of the three complement pathways with deposition of C5b-C9 as a common read-out. Briefly, wells of microtitre strips are coated with specific activators of each of the three complement pathways. Human serum is diluted in diluent containing specific blocker to ensure that only the respective pathway is activated. C1INH of the invention or its plasma-derived counterpart is further added in a concentration ranged between 0 and 75 mol, incubated for 30 minutes at room temperature and added to the wells. During a subsequent incubation of the diluted human serum in the well for 60 minutes at 37° C., complement is activated by the specific coating. The wells are then washed and C5b-C9 formed is detected with a specific alkaline phosphatase labelled anti C5b-C9 antibody. After a further washing step, detection of specific antibodies is obtained by incubation with alkaline phosphatase substrate solution. The amount of complement activation correlates with the colour intensity and is measured in terms of absorbance (optical density OD). Using this kit, both recombinant human C1INH (rhC1INH) of the invention and plasma-derived C1INH (pdC1NH) were found to have similar inhibiting capacities for the classical pathway. However, the C1INH of the invention was found to have approximately 20% more inhibiting capacity for the MBL pathway than plasma-derived C1INH (see example 3).

Therefore accordingly, in this preferred embodiment, the different glycosylation of the C1INH for use in the present invention results in a higher affinity for a MBP as compared to its plasma derived counterpart, which results in a more efficient inhibition of MBP, leading to a more efficient inhibition of the lectin pathway. More efficient inhibition of the lectin pathway preferably means at least 5% more inhibition, even more preferably at least 10% more inhibition, even more preferably at least 15% more inhibition even more preferably at least 20% even more preferably at least 25% even more preferably at least 30% even more preferably at least 35% even more preferably at least 40% even more preferably at least 45% even more preferably at least 50% even more preferably at least 55% even more preferably at least 60% even more preferably at least 65% even more preferably at least 70% even more preferably at least 75% even more preferably at least 80% even more preferably at least 85% even more preferably at least 90% even more preferably at least 95% and most preferably at least 98% more inhibition. The activation of the lectin pathway is preferably measured by the Wielisa kit as described above.

The method of the invention may be applied to prevent, reduce or treat any type of ischemia and reperfusion injury. Preferably, the method of the invention is applied wherein the ischemia and reperfusion injury is known to arise at least in part, more preferably mostly via the lectin pathway. For myocardial ischemia and reperfusion injury (J Immunology 2005, 175: 541-546), renal ischemia-reperfusion injury (Am J. Pathol. 2004 165(5):1677-88), gastrointestinal ischemia reperfusion injury (J. Immunol. 2005 15:174(10):6373-80), and for stroke (deSimoni et al, 2004 Am J. Pathol. 164:1857-63) it has been shown that reperfusion injury arises mostly via the lectin pathway and hardly via the classical pathway. Hence, a C1INH of the invention preferably is a more potent inhibitor of the lectin pathway as compared to its natural plasma derived counterpart. Preferably a C1INH of the invention is a more potent in vivo inhibitor of the lectin pathway in man as compared to its natural plasma derived counterpart.

Unlike the experimental model used in the Examples herein, the occurrence of ischemia in real life often is an unforeseen event. Therefore administration of C1INH prior to the occurrence of ischemia and/or subsequent reperfusion is not generally a feasible option and inevitably in practice C1INH will have to be administered some time if not several hours after ischemia and/or subsequent reperfusion. This, however, seriously limits the therapeutic usefulness of conventional plasma derived C1INH because it is mostly ineffective when administered subsequent to ischemic reperfusion and only has a very small time window for therapeutic efficacy (see FIG. 2 and deSimoni et al, 2004 Am J. Pathol. 164:1857-63). In contrast, a C1INH for use in the present invention as defined above, is still able to exert its neuroprotective effects also when injected at least 1 hour after ischemia or after the onset of ischemia and/or 30 minutes after the start of the reperfusion. Therefore, in a preferred embodiment of the method for the prevention, reduction or treatment of at least one of unforeseen or foreseen occurrence of ischemia and reperfusion injury, the C1INH of the invention is administered at least at the end or after the ischemic period, i.e. when the ischemic tissue is reperfused. More preferably, the C1INH of the invention is administered at least 10, 15, 20, 30, 45, 60, 90 or 120 minutes after the ischemic period or after the start of reperfusion. Preferably, the C1INH of the invention is administered no more than 24, 12, 6, 4 or 3 hours after ischemia or after the onset of ischemia and/or reperfusion. In another preferred embodiment, the C1 inhibitor is administered at least 3 hours after ischemia or after the onset of ischemia and/or reperfusion, preferably at least 6 hours, more preferably at least 9 hours, even more preferably at least 18 hours.

In one preferred embodiment, the method is applied to prevent, reduce or treat an unforeseen, sudden or acute occurrence of ischemic reperfusion. Conditions and disorders associated with an unforeseen, sudden or acute occurrence of ischemic reperfusion injury include but are not limited to ischemic reperfusion injury after acute myocardial infarction (AMI), after stroke, including perinatal stroke, after hemorrhagic shock, after intestinal ischemia, after emergency coronary surgery for failed percutaneous transluminal coronary angioplasty (PCTA), after any vascular surgery with blood vessel cross clamping (e.g. of aorta, leading to skeletal muscle ischemia), or after pancreatitis after manipulation of pancreatic or bile duct (ERCP). In such instances the C1INH of the invention preferably is administered at least 1, 5, 10, 15, 20, 30, 45, 60, 90 or 120 minutes after the acute myocardial infarction (AMI), after stroke, including perinatal stroke, after hemorrhagic shock, after intestinal ischemia, after emergency coronary surgery for failed percutaneous transluminal coronary angioplasty (PCTA), after any vascular surgery with blood vessel cross clamping (e.g. of aorta, leading to skeletal muscle ischemia), or after pancreatitis after manipulation of pancreatic or bile duct (ERCP). Alternatively, the time of administering the C1INH of the invention may be defined as preferably at least 1, 5, 10, 15, 20, 30, 45, 60, 90 or 120 minutes after the start of reperfusion.

In addition, unforeseen ischemic reperfusion injury is preferably defined as an ischemic reperfusion injury wherein a therapy or surgery induces a reperfusion but not an ischemia. Such therapy or surgery include but not limited to:
  pharmacological thrombolysis, including intravenous and endovascular therapies for stroke, acute coronary syndromes, peripheral arterial occlusion, pulmonary embolus, renal artery occlusion,
  mechanical thrombolysis, e.g. percutaneous coronary intervention, peripheral arterial angioplasty, visceral arterial angioplasty,
  coronary artery bypass grafting,
  carotid endarterectomy,
  mesenteric ischemia,
  shock including hemorrhagic, cardiogenic, neurogenic, analphylactic,
  flap-failure, e.g. plastic surgery,
  re-implantation of digits and limbs,
  strangulated bowel.

Alternatively, in another preferred embodiment, the method is applied to prevent, reduce or treat a foreseen occurrence of ischemic reperfusion. A foreseen occurrence of ischemia reperfusion injury preferably includes a setting in which a therapy or surgery induce both an ischemia and subsequently a reperfusion. A non-limiting list is given below of therapy or surgery in which there is an induced temporary period of no or low blood flow, i.e. ischemia or hypoxia, followed by reperfusion:
  cardiopulmonary bypass,
  aneurysm repair, including aortic, cerebral,
  carotid endarterectomy in which a clamp is used during the surgery,
  deep hypothermic circulatory arrest,
  tourniquet use, i.e. in trauma settings,
  solid organ transplantation,
  any other iatrogenic disruption of blood flow.

In addition, conditions and disorders associated with a foreseen occurrence of ischemic reperfusion injury include but are not limited to ischemic reperfusion injury after organ transplantation (lung, liver, kidney, heart), after any vascular surgery with blood vessel cross clamping (e.g. of aorta, leading to skeletal muscle ischemia), or after pancreatitis after manipulation of pancreatic or bile duct (ERCP), after or during extra corporal circulation (ECC).

In a preferred embodiment of the method for the prevention, reduction or treatment of at least one of foreseen occurrence of ischemia and reperfusion injury, the C1INH of the invention is administered at least at the end or after the ischemic period, i.e. when the ischemic tissue is reperfused. More preferably, the C1INH of the invention is administered at least 10, 15, 20, 30, 45, 60, 90 or 120 minutes after the ischemic period or after the start of reperfusion. Preferably, the C1INH of the invention is administered no more than 24, 12, 6, 4 or 3 hours after ischemia or after the onset of ischemia and/or reperfusion. In another preferred embodiment, the C1 inhibitor is administered at least one hour after ischemia or after the onset of ischemia and/or reperfusion, 3 hours after ischemia or after the onset of ischemia and/or reperfusion, preferably at least 6 hours, more preferably at least 9 hours, even more preferably at least 18 hours.

Alternatively, in another aspect of the invention, a method is provided for the prevention, reduction or treatment of at least one of foreseen occurrence of ischemia and reperfusion injury, wherein the C1I NH of the invention is administered before or during the ischemia and reperfusion. The skilled person will understand that depending upon the plasma half life of the C1INH of the invention, the earliest possible time point, wherein the C1INH of the invention may be administered may be adjusted to obtain the best possible result.

According to one preferred embodiment, the C1INH of the invention is continuously administered to a subject in the need thereof and/or in case of an organ transplantation to the organ to be transplanted. The organ to be transplanted is preferably conserved in a composition with a suitable medium and suitable amount of C1INH.

Alternatively or in combination with former preferred embodiment, before the occurrence of a foreseen type of ischemia and reperfusion injury preferably means that the administration is performed at the most 3 hours before at least one foreseen occurrence of ischemia and reperfusion injury, preferably at the most 2 hours, more preferably at the most one hour, and most preferably at the most 30 minutes.

A subject in the need thereof is a subject wherein a foreseen occurrence of ischemia and reperfusion injuries may occur. Foreseen occurrence of ischemia and reperfusion injuries have been already described herein.

The administration of the C1INH before the foreseen occurrence of ischemia and reperfusion injury is attractive since it may prevent the occurrence of most if not all damages associated with the ischemia and reperfusion injury the same way as presented when the C1INH is administered after the occurrence of ischemia and reperfusion injury, if not better.

In a more preferred embodiment, the method is applied to an unforeseen occurrence of ischemic reperfusion. Even more preferably, an ischemic reperfusion injury occurring after a stroke or a perinatal stroke. In these types of unforeseen occurrence of ischemic reperfusion, we demonstrated that the C1 inhibitor of the invention exerts a neuroprotective effect in the ischemic penumbra. The ischemic penumbra preferably means the hippocampus and/or cortex. A neuroprotective effect preferably means that neurodegeneration is counteracted in the hippocampus and/or cortex after treatment with the C1 inhibitor of the invention up to 3 hours after the onset of ischemia in the hippocampus and up to 9 hours after the onset of ischemia in the cortex. More preferably, neurodegeneration is counteracted up to 4, 5, 6 hours or more in the hippocampus and up to 10, 11, 12 hours or more in the ischemia. Neurodegeneration is preferably assessed as in example 2: brain sections are stained with a marker specific for neuronal degeneration, preferably Jade (Schmued L C, et al, reference 4) and analyzed by fluorescent microscopy. Using this method, counteraction of neurodegeneration means at least 2% less stained cells are visualized in the treated sample compared to the untreated sample. Preferably, counteraction of neurodegeneration means at least 5% less stained cells, at least 7%, at least 10%, at least 15%, at least 20%, at least 25%, at least 30%, at least 35%, at least 40% or more.

Alternatively or in combination with former mentioned embodiment, the use of the C1 inhibitor exerts a reduction of the lesion induced by the ischemia and/or reperfusion. More preferably, when the ischemic reperfusion injury occurred after a stroke or a perinatal stroke, the use of the C1 inhibitor of the invention exerts a reduction of the infarct size. Even more preferably, the infarct size is quantified as presented in example 2. Even more preferably, using this quantification method, at least 3 hours after the onset of ischemia, a reduction of at least 10% of the infarct size is reached, even more preferably at least 20%, even more preferably at least 40%, even more preferably at least 60%, even more preferably at least 70%, even more preferably at least 80%, and most preferably at least 90%.

A C1INH for use in the methods of the invention may be part of or combined with state of the art pharmaceutical compositions. These pharmaceutical compositions typically comprise the C1INH and a pharmaceutically acceptable carrier or excipient. These pharmaceutical compositions may be administered in a number of ways depending on whether local or systemic treatment is desired, the area to be treated and the stability of the active compound. Suitable formulations will depend on the method of administration. The pharmaceutical composition is preferably administered by par-enteral administration, such as for example by intravenous, intra-arterial, subcutaneous, intraperitoneal or intramuscular injection or infusion; or by intrathecal or intracranial administration. In a preferred embodiment it is administered by intravenous infusion. Suitable formulations for parenteral administration are known in the art and are typically liquid formulations. C1INH preparations for parental administration must be sterile. Sterilization is readily accomplished by filtration through sterile filtration membranes, prior to or following lyophilization and reconstitution. C1INH preparations may be administered continuously by infusion or by bolus injection. Liquid C1INH formulations may for example be administered by an infusion pump. A typical composition for intravenous infusion could be made up to contain 100 to 500 ml of sterile 0.9% NaCl or 5% glucose optionally supplemented with a 20% albumin solution and 100 to 500 mg of the C1INH. A typical pharmaceutical composition for intramuscular injection would be made up to contain, for example, 1-10 ml of sterile buffered water and 1 to 250 mg of the C1INH of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

The effective dose, i.e. effective concentration and frequency, of the C1INH when used in the methods of the invention will depend on the specific pharmaceutical composition which is used, the severity of the condition and the general state of the patient's health. In general, the effective dose of a pharmaceutical composition which is based on a C1INH for use in the methods of the invention may be found by routine optimisation. A suitable starting point is the dose which is used for the equivalent pharmaceutical composition which is based on plasma-derived C1INH. A great advantage of a pharmaceutical composition of the invention is that a high initial dose may be used in treatment, which enhances the likelihood of successful treatment. This high initial dose is possible because the C1INH in the pharmaceutical composition of the invention shows a faster clearance than its natural counterpart. In particular for the treatment of acute cases, a high initial dose of the C1INH of the invention may be advantageous. This high initial dose may be at least 1.5, at least 2, 3 or 4 times the dose of the natural occurring counterpart which would be administered.

In a preferred embodiment, C1INH of the invention is administered intravenously at a dose of more than 50, 100, 200, 400, 600, 800, or 1000 U/kg body weight of the individual, preferably in the range of 50-2000, 100-1000, 200-800, 400-700 or 500-700 U/kg body weight of the individual. One unit (U) of C1INH is the amount of C1INH present in 1 milliliter of human blood. One such unit corresponds to approximately 275 microgram plasma derived C1INH. Assuming a molecular weight of 110,000 dalton, the concentration in human plasma of C1INH is 2.5 micromol per liter (Nuijens et al. (1989), J. Clin. Invest. 84:443).

In a further preferred embodiment of the method of the invention the pharmaceutical composition further contains a thrombolytic agent or is for use in combination with a thrombolytic agent or after subsequent treatment with such agent. A thrombolytic agent is herein understood to mean an agent (drug) that is able to dissolve a blood clot (thrombus) and reopen an artery or vein. Thrombolytic agents are usually serine proteases and convert plasminogen to plasmin which breaks down the fibrinogen and fibrin and dissolves the clot. Preferred thrombolyic agents include reteplase (r-PA or Retavase), alteplase (t-PA or Activase), urokinase (Abbokinase), prourokinase, anisoylated purified streptokinase activator complex (APSAC), and streptokinase.

In a further aspect, particularly for jurisdictions other than the USA, the invention pertains to the use of a C1INH of the invention as defined herein above for the manufacture of a medicament for the prevention, reduction or treatment of reperfusion injury in accordance with any of the methods defined herein above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

DESCRIPTION OF THE FIGURES

FIG. 16 Effect of rhc1INH and pdC1INH on activation of both the classical and MBL pathway of complement activation. Increasing doses of rhC1INH or pdC1INH was added to two different samples of normal human serum. As a control, the buffer in which rhC1INH is dissolved (20 mM citrate, 0.19 M sucrose pH 6.8; 0.22 µm filtered) was taken along in the same dilutions as rhC1INH. Readout was deposition of C5b-9 and the percentage complement activation was calculated per measurement with this formula: (Sample−NC)/(PC−NC)×100. PC is set at 100%. Results shown are the mean SD of 3 independent verdunning at each concentration tested.

EXAMPLES

Example 1

Figure 1:
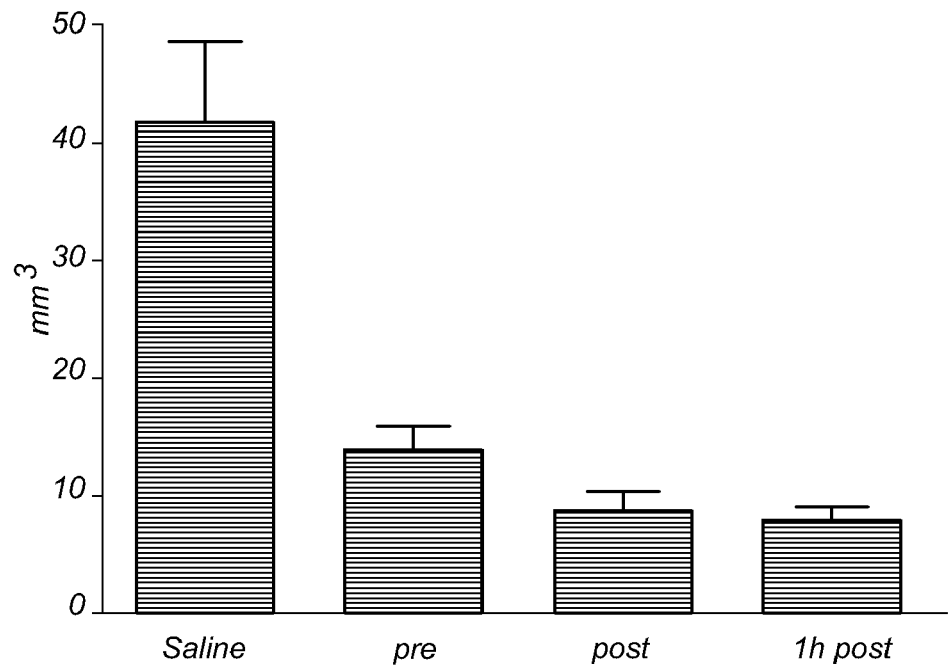
FIG. 1 Assessment of infarct size forty-eight hours after ischemia in mice treated with saline or with 15 U rhC1INH (recombinant human C1INH, see Example 1.2) per mouse pre, post and 1 h post ischemia.

Previous experiments showed that a single dose of rhC1INH (15 U/mouse) administered at the beginning of the ischemic period, significantly reduces ischemic volume, as assessed 48 hours after ischemia in our mouse model of cerebral focal ischemia in a manner very similar to plasma derived C1INH. In this Example we have explored the time window of efficacy for rhC1INH neuro-protective activity on the ischemic volume and functional deficits. We have also studied the effect of rhC1INH on seven-days outcome by assessing the neurodegeneration and glial response.
1. Methods
1.1 Transient Focal Cerebral Ischemia Ischemia was achieved by middle cerebral artery occlusion (MCAO) as previously described (De Simoni et al., 2003 and 2004, supra). Anesthesia was induced by 5% isoflurane in $N_2O/O_2$ (70/30%) mixture and maintained by 1.5-2% isoflurane in the same mixture. To confirm the adequacy of the vascular occlusion in each animal, blood flow was measured by laser doppler flowmetry (Transonic BLF-21) using a flexible 0.5 mm fiberoptic probe (Transonic, Type M, 0.5 mm diameter) positioned on the brain surface and secured with impression material on the skull at the following coordinates: AP=−1 mm; L=−3.5 mm. Briefly, the right common carotid artery was exposed and a siliconized filament (7-0), was introduced into the internal carotid artery through an incision performed on the common carotid artery and advanced to the anterior cerebral artery so as to block its bifurcation into the anterior cerebral artery and the MCA. The filament was advanced until a>70% reduction of blood flow, compared to preischemic baseline, was observed. After 30 min of ischemia, blood flow was restored by carefully removing the nylon filament.
1.2 Drug Treatment Mice received a single iv injections of rhC1INH at the dose of 15 U/mouse in 150 µl or the same volume of saline at different time from ischemia:
  at the beginning of ischemic period (rhC1INH-pre).
  at the end of ischemic period (rhC1INH-post).
  one hour after the beginning of the ischemic period (rhC1INH 1 h-post).
rhC1INH used in this study was produced in transgenic rabbits that express human C1INH in their mammary glands and purified from the milk obtained from these animals as described in WO 01/57079.
1.3 Evaluation of Neurological Deficits Forty-eight hours after ischemia, each mouse was rated on two neurological function scales unique to the mouse, by a trained investigator blinded to the experimental conditions. For general deficits mice were scored from 0 to 28 in each of the following categories: hair, ears, eyes, posture, spontaneous activity, epileptic behavior. For focal deficits mice were scored from 0 to 28 in each of the following categories: body symmetry, gait, climbing, circling behavior, front limb symmetry, compulsory circling, sensory response. Data are expressed as median and $25^{th}$ to $75^{th}$ percentiles.

1.4 Quantification of Infarct Size

Forty-eight hours after ischemia, mice were deeply anesthetized with Equitensin (120 µl/mice, ip) and transcardially perfused with 30 ml of PBS 0.1 mol/l, pH 7.4, followed by 60 ml of chilled paraformaldheyde (4%) in PBS. After carefully removing the brains from the skull, they were transferred to 30% sucrose in PBS at 4° C. overnight for cryoprotection. The brains were then rapidly frozen by immersion in isopentane at −45° C. for 3 min before being sealed into vials and stored at −70° C. until use. For lesion size determination, 20 µm coronal brain sections were cut serially at 240 µm intervals and stained with neutral red (Neutral Red Gurr Certistain, BDH, England). On each slice, infracted areas were assessed blindly and delineated by the relative paleness of histological staining. The infracted area was determined by subtracting the area of the healthy tissue in the ipsilateral hemisphere from the area of the contralateral hemisphere on each section. Infarct volumes were calculated by the integration of infracted areas on each brain slice as quantified with computer-assisted image analyzer and calculated by Analytical Image System.
1.5 Open Field Test Seven days after ischemia mouse behavior was evaluated by the open field test. This test may be useful to dectect anxiety and exploratory behavior, and locomor activity in long-term ischemic mice. The open filed consisted of a plastic box (41×41×41 cm) containing 4 different objects. The area of the open field was divided into a 28×28 cm central zone and the surrounding border zone. Mice were individually placed into the centre of the open field and their behavior was observed for 5 minutes by an investigator blinded to the experimental conditions. The number of inside crossings (mainly related to anxiety behavior), outside crossings (mainly related to motor activity), rears (mainly related to exploratory behavior) and contacts with objects (mainly related to sensory/motor activity) was counted.
1.6 Neuronal Count Seven days after ischemia, mice were transcardially perfused as previously described. For neuronal count determination, 20 µm coronal brain sections were cut serially at 640 µm intervals and stained with cresyl violet (Cresyl Violet acetate, Sigma, St. Louis, Mo.). Three 20 µm sections from ipsi- and controlateral hemispheres were selected for neuronal count. The first section was at stereotaxic coordinates anteroposterior +0.86 from bregma. The amount of neuronal loss was calculated by pooling the number of viable neurons in the three sections of both hemispheres and expressed as percentage of controlateral hemisphere. An Olympus BX61 microscope, interfaced with Soft Imaging System Colorview video camera and AnalySIS software was used. The quantitative analysis was performed at 40× magnification by an investigator blinded to the treatment.
1.7 Immunohistochemistry for Astrocytes and Microglia Seven days after ischemia twenty-µm-thick coronal sections from transcardially perfused ischemic mice were prepared and used for assessment of astrocytes and microglia/macrophages immunostaining. Briefly, the sections were rinsed for 30 minutes in 0.4% Triton X-100 in 0.1 mol/L PBS followed by 15 minutes in 0.1% Triton X-100 and 3% normal goat serum (NGS) in PBS. The sections were then incubated overnight with antibody for astrocytes and microglia (anti-GFAP 1:1500, Chemicon; anti-CD11b 1:250, kindly gift by Dr. A. Doni, Mario Negri Institute). The next day, the sections were washed in PBS and incubated with biotinylated secondary antibody for 1 h, washed and incubated with avidin-biotin-peroxidase. After reacting with 3-3-diaminobenzidine tetrahydrochloride the sections were washed, dried, dehydratate through graded alcohols, fixed in xylene and cover-slipped using DPX mountant before light microscopy analysis.

2. Results
2.1 Time-window of Efficacy
2.1.1 Evaluation of Neurological Deficits Neurological deficits were evaluated in ischemic mice receiving rhC1INH or saline 48 h after ischemia. A slight, although not significant, decrease in every group of rhC1INH-treated mice was observed compared to saline-treated ischemic mice (rhC1INH-pre: 9 and 12; rhC1INH-post: 7 and 11; rhC1INH 1 h-post: 9 and 13, saline: 10 and 12.5, median of general and focal deficits, respectively) (data not shown).

2.1.2 Assessment of Infarct Size

Forty-eight hours after ischemia rhC1INH-treated mice showed a marked reduction of the ischemic volume, at 15 U/mouse-pre, -post and 1 h-post doses ($13.67\pm2.59$ mm$^3$, $9.06\pm0.77$ mm$^3$ and $8.24\pm1.00$ mm$^3$, respectively), compared to saline-treated mice ($41.51\pm7.01$ mm$^3$) (FIG. 1, data are expressed as mean $\pm$SEM).

2.2 Seven-days Outcome
2.2.1 Open Field Test

Ischemia induced a significant reduction in the number of rears compared to naïve animals while in the rhC1INH-treated group this parameter was not different from non-ischemic mice. The other parameters evaluated did not show any difference among the three groups.

2.2.2 Neuronal Count

To evaluate if the protective effect of rhC1INH is long lasting, we assessed the neuronal loss 7 days after induction of ischemia and treatment with the drug. The results show that rhC1INH protective effect is still present at this time: $14\%\pm2.18\%$ versus $4\%\pm1.24\%$ mean of saline- and rhC1INH-treated mice, respectively (data not shown).

2.2.3 Immunohistochemistry for Microglia/macrophages and Astrocytes

Seven days after ischemia a large amount of activated microglia and infiltrated macrophages were observed in the lesioned hippocampus and striatum of ischemic mice receiving saline (data not shown). Fifteen units of rhC1INH-pre were able to counteract this activation and infiltration in both the areas considered (data not shown). The ipsilateral hippocampus of saline-treated ischemic mice showed a slight astrocytosis which was not different from that observed in rhC1INH-ischemic mice (data not shown). Other brain areas did not show any relevant astrocytic activation in either groups.

3. Conclusions

Figure 2:
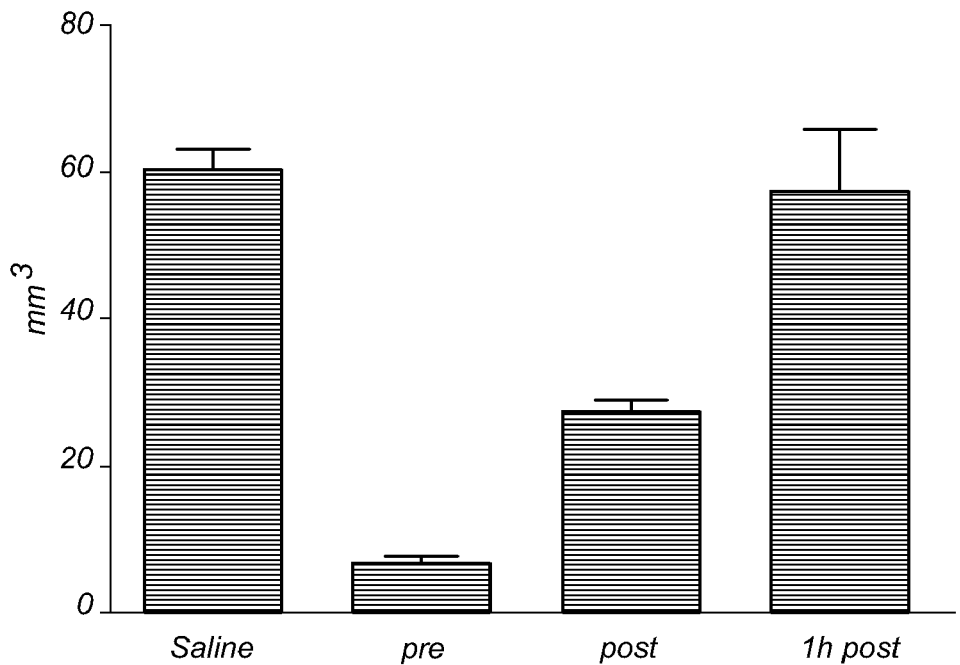
FIG. 2 Assessment of infarct size twenty-four hours after ischemia in mice treated with saline or with 15 U plasma derived hC1INH per mouse pre, post and 1 h post ischemia.

The present data show that rhC1INH at the dose of 15 U/mouse is similarly effective in reducing the ischemic volume when given at the beginning (-pre) or at the end of ischemic period (-post, i.e. at reperfusion). More importantly the inhibitor is able to exert its neuroprotective effects also when injected 1 hour after the onset of ischemia (1 h-post). Furthermore, the protective action of rhC1INH is still present 7 days after ischemia. These results are in sharp contrast with plasma derived hC1INH which when injected 1 hour after ischemia has nearly completely lost the ability to exert neuroprotective effects (see FIG. 2).

The main results of this study are the following:
1. the half life of rhC1INH in mouse plasma is about 3 hours (at a dose of 15 U/mouse). The good correlation between antigen and functional activity indicates that the recombinant protein circulates in plasma in its active form only; it is possible that tissue distribution contributed to the reduction of plasma levels.
2. rhC1INH, at the dose of 15 U/mouse-pre is very effective in reducing the ischemic volume (reduction of 69%).
3. rhC1INH at the dose of 15 U/mouse is able to clearly reduce the number of degenerating neurons in the hippocampus as assessed by Fluoro-Jade staining thus indicating that the reduction in ischemic volume is due to sparing of neurons.
4. rhC1INH is similarly effective in reducing ischemic volume when given at the beginning (-pre), at the end of the ischemic period (-post, i.e. at reperfusion) or 1 hour after the onset of ischemia (1 h-post, i.e. 30 min from beginning of reperfusion). Thus rhC1INH has a wider time-window of efficacy than pdC1INH (that is no more effective when given 1 h after ischemia).
5. the neuroprotective effect of rhC1INH-pre dose is long-lasting, as showed by neuronal counting performed 7 days after the beginning of ischemia.
6. rhC1INH, induced a slight improvement of general and focal deficits assessed 48 hours after ischemia. This finding is similar to what observed with pdC1INH. In order to evaluate the effect of rhC1INH on long-term behavioral outcome, we analyzed mouse behavior by open field test. Seven days after ischemia the rearing behavior shows a significantly lower score in the ischemic compared to naïve mice. This decrease is not present in rhC1INH treated mice whose score is not different from control mice.
7. rhC1INH is able to counteract the activation/recruitment of microglia/macrophages in ischemic mice brain as assessed both at early (48 h) and at late (7 days) time points. These cells are an index of the inflammatory response of the brain tissue.
8. The strong astrocytic response elicited by ischemia at 48 h is dampened by rhC1INH. The astrocytic activation is markedly decreased at 7 days in both experimental groups and no difference between saline- and rhC1INH-treated mice could be observed.

Example 2

Study on the Neuroprotective Action of rhC1-INH in Mouse Models of Focal Cerebral Ischemia We have previously demonstrated that 15 U of rhC1-INH have a marked neuroprotective action in a model of murine cerebral ischemia/reperfusion also when administrated 1 hour after the onset of ischemia/reperfusion, at variance with pdC1-INH that, at this time of post-treatment, is no longer effective. This neuroprotection is long-lasting, in fact seven days after ischemia and treatment, ischemic brains of mice treated with rhC1-INH still show a decreased infarct size. In the following experiments we have determined the time window of efficacy (beyond 1 hour post) and the dose-response of rhC1-INH neuroprotective activity on the ischemic volume. In addition we have performed a direct comparison among pdC1-INH, rabbit and cow rhC1-INH (at the most effective dose and time-points for rabbit rhC1-INH) using the same protocol.

Methods
Animals

Procedures involving animals and their care was conducted in conformity with institutional guidelines that are in compliance with national (D.L. n.116, G.U. suppl. 40, 18 Feb. 1992) and international laws and policies (EEC Council Directive 86/609, OJ L 358,1; Dec. 12, 1987; NIH Guide for the Care and Use of Laboratory Animals, U.S. National Research Council 1996). Male C57B1/6 mice (26-28 g, Charles River, Calco, Italy) were housed 5 per cage and kept at constant temperature (21±1° C.) and relative humidity (60%) with regular light/dark schedule (7 am-7 pm). Food (Altromin pellets for mice) and water available ad libitum.

Transient Focal Cerebral Ischemia

Ischemia was achieved by middle cerebral artery occlusion (MCAO) as previously described[1,3]. Anesthesia was induced by 5% isoflurane in NaO/Oa (70/30%) mixture and maintained by 1.5-2% isoflurane in the same mixture. To confirm the adequacy of the vascular occlusion in each animal, blood flow was measured by laser doppler flowmetry (Transonic BLF-21) using a flexible 0.5 mm fiberoptic probe (Transonic, Type M, 0.5 mm diameter) positioned on the brain surface and secured with impression material on the skull at the following coordinates: AP=−1 mm; L=−3.5 mm. Briefly, the right common carotid artery was exposed and a siliconized filament (7-0) was introduced into the internal carotid artery through an incision performed on the common carotid artery and advanced to the anterior cerebral artery so as to block its bifurcation into the anterior cerebral artery and the MCA. The filament was advanced until a>70% reduction of blood flow, compared to preischemic baseline, was observed. After 30 min of ischemia, blood flow was restored by carefully removing the nylon filament.

Drug Treatment

Mice received a single iv injections of C1-INH (rabbit rhC1-INH, cow rhC1-INH or pdC1-INH) at different doses at different times from ischemia. Control mice received the same volume of saline.

Evaluation of Neurological Deficits.

Forty-eight hours after ischemia, each mouse was rated on two neurological function scales unique to the mouse, by a trained investigator blinded to the experimental conditions. For general deficits mice were scored from 0 to 28 in each of the following categories: hair, ears, eyes, posture, spontaneous activity, epileptic behavior. For focal deficits mice were scored from 0 to 28 in each of the following categories: body symmetry, gait, climbing, circling behavior, front limb symmetry, compulsory circling, sensory response. Data are expressed as median and percentiles.

Quantification of Infarct Size

Forty-eight hours after ischemia, mice were deeply anesthetized with Equitensin (120 jil/mice, ip) and transcardially perfused with 30 ml of PBS 0.1 mol/l, pH 7.4, followed by 60 ml of chilled paraformaldheyde (4%) in PBS. After carefully removing the brains from the skull, they were transferred to 30% sucrose in PBS at 4° C. overnight for cryoprotection. The brains were then rapidly frozen by immersion in isopentane at −45° C. for 3 min before being sealed into vials and stored at −70° C. until use. For lesion size determination, 20fjm coronal brain sections were cut serially at 240(j,m intervals and stained with neutral red (Neutral Red Gurr Certistain, BDH, England). On each slice, infracted areas were assessed blindly and delineated by the relative paleness of histological staining. The infracted area was determined by subtracting the area of the healthy tissue in the ipsilateral hemisphere from the area of the contralateral hemisphere on each section. Infarct volumes were calculated by the integration of infracted areas on each brain slice as quantified with computer-assisted image analyzer and calculated by Analytical Image System.

Assessment of Neurodegeneration

The presence of neurodegeneration was evaluated on 20 jam thick sections by staining with Fluoro-Jade[4], a marker for neuronal degeneration. Briefly, sections were dried and rehydrated in ethanol (100%-75%) and distilled water. Then, they were incubated in 0.06% potassium permanganate for 15 minutes, washed in distilled water and transferred to 0.001% Fluoro-Jade staining solution for 30 minutes. After staining, the sections were rinsed in distilled water, dried, immerse in xylene and coverslipped using DPX mountant (BDH, Poole, UK) before fluorescent microscopy analysis.

Results

Time-Window of Efficacy in Transient Ischemia

Figures 3, 4:
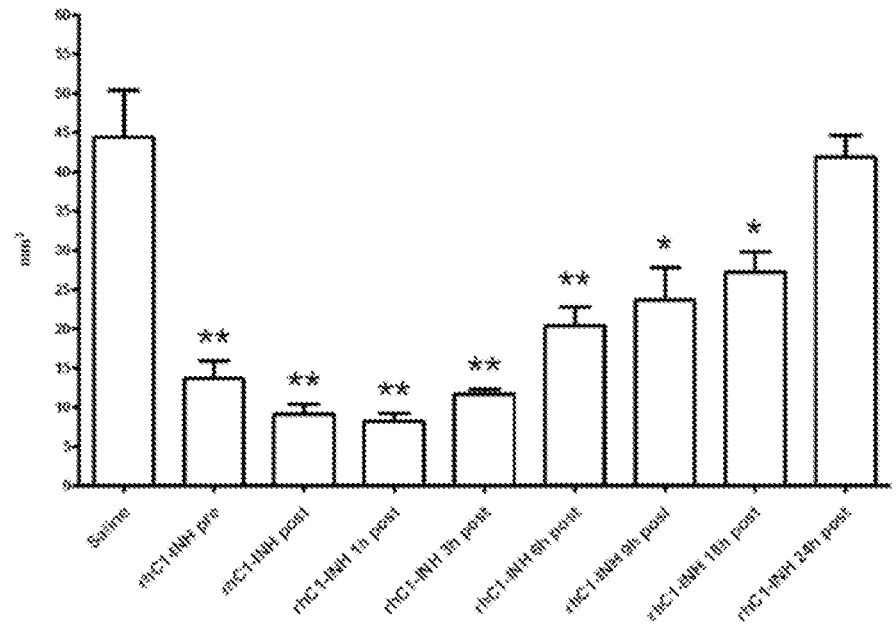
FIG. 3 Infarct volume assessed 48 h after ischemia in mice receiving saline or 15 U/mouse of rabbit rhC1-INH at different time points from the beginning of ischemia. Data are expressed as mean ±SEM (n=6 mice per group). *P<0.05, **P<0.01 versus saline, one way ANOVA and Dunnett as post-hoc test.
FIG. 4 Semi-quantitative evaluation of Fluoro-Jade staining. −=no positivity, +=low positivity, ++=intermediate positivity, +++=high positivity.
Figure 5:
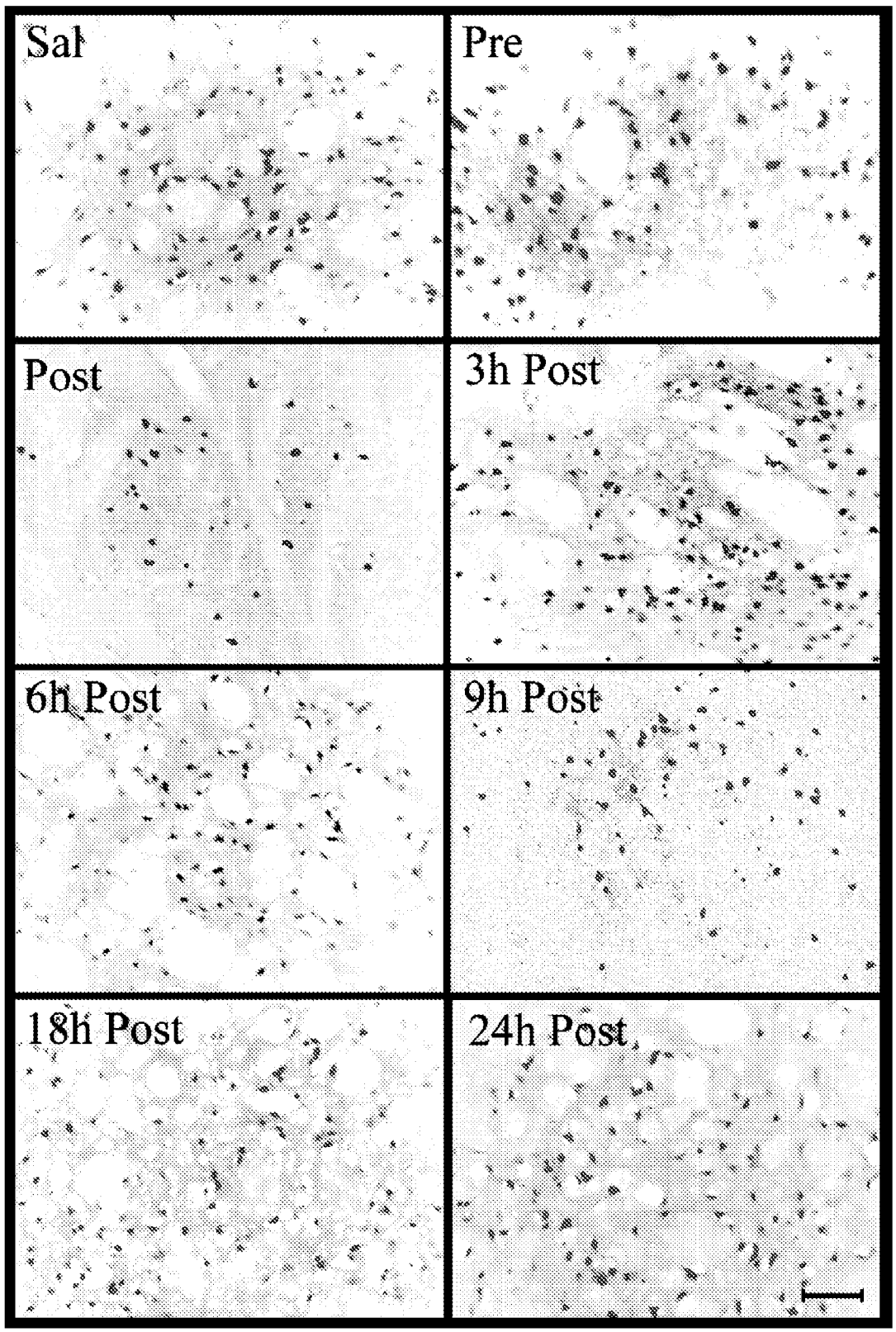
FIG. 5 Representative images of neurodegeneration by Fluoro-Jade staining in the striatum of ischemic mice receiving saline or 15 U/mouse of rabbit rhC1-INH at different time points from the onset of ischemia. Bar: 100 µm.
Figure 6:
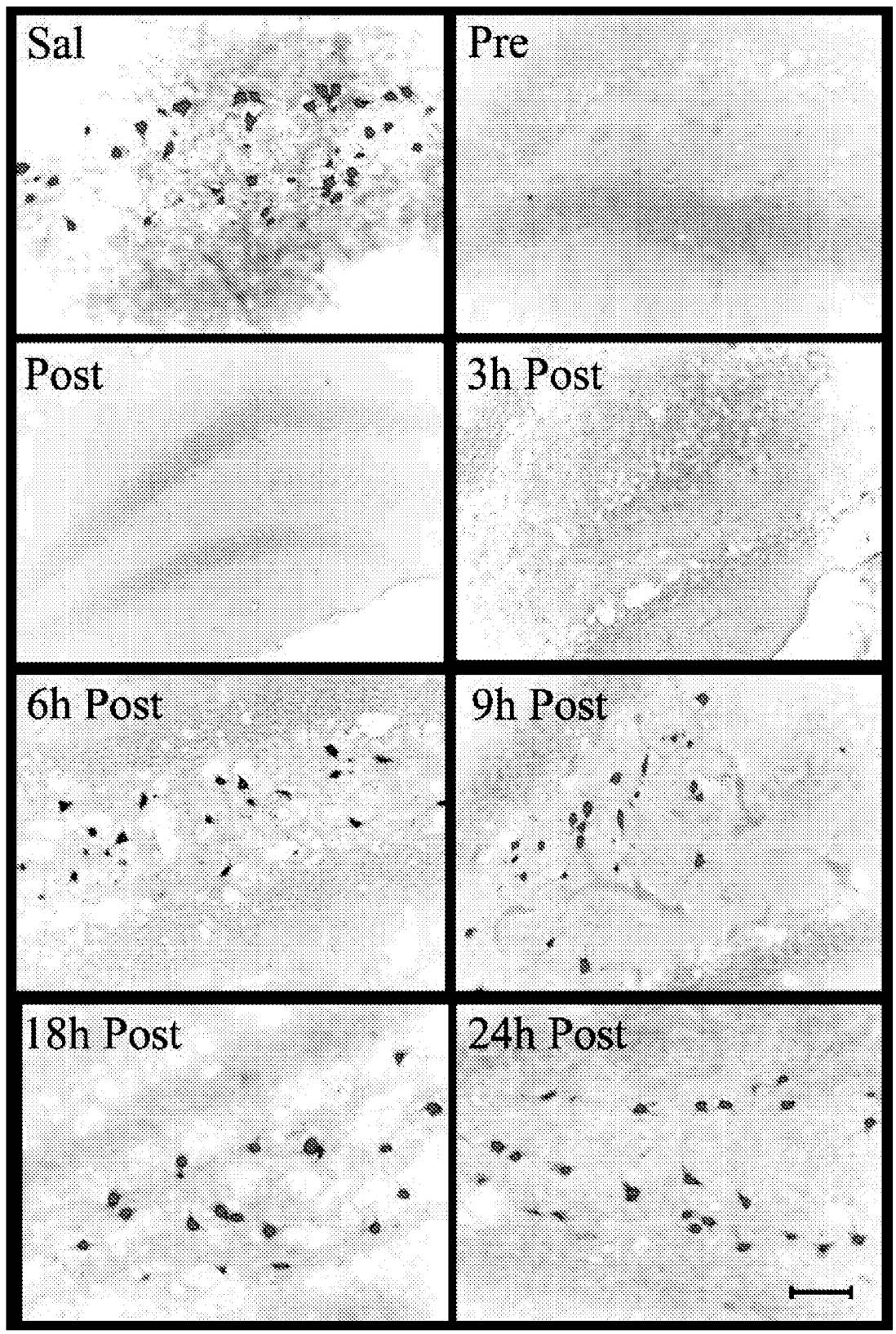
FIG. 6 Representative images of neurodegeneration by Fluoro-Jade staining in the dentate gyrus of ischemic mice receiving saline or 15 U/mouse of rabbit rhC1-INH at different time points from the onset of ischemia. Bar: 100 µm.
Figure 7:
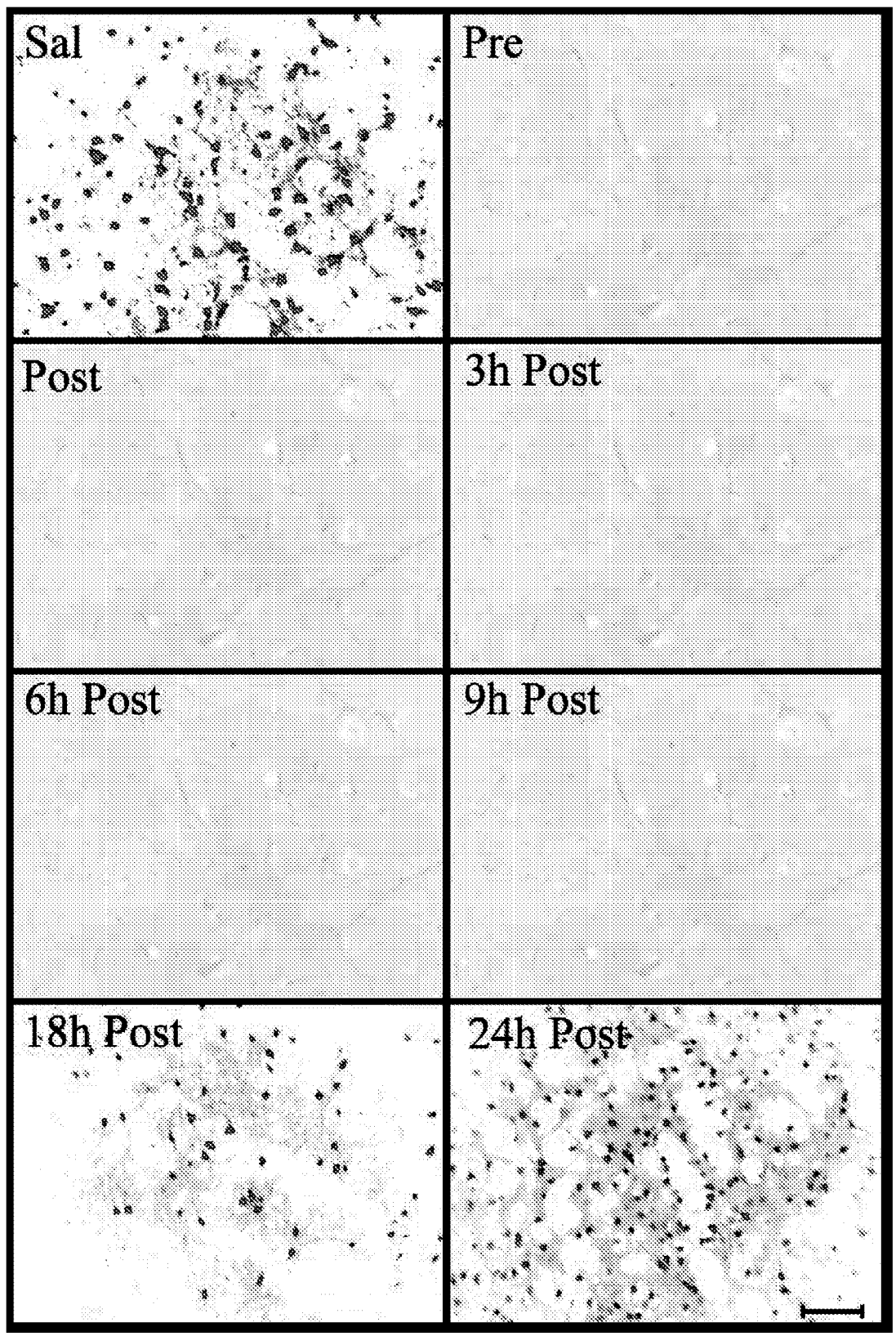
FIG. 7 Representative images of neurodegeneration by Fluoro-Jade staining in the cortex of ischemic mice receiving saline or 15 U/mouse of rabbit rhC1-INH at different time points from the onset of ischemia. Bar: 100 µm.

In order to evaluate the time-window of efficacy, 15 U of rabbit rhC1-INH or saline were given at 3, 6, 9, 18 and 24 hours from the beginning of ischemia. Forty-eight hours later, ischemic mice treated with rabbit rhC1-INH 3 and 6 hours after the onset of ischemia showed a marked decrease of ischemic volume ($11.71 \pm 0.63$ mm$^3$ and $20.38 \pm 2.37$ mm$^3$, respectively) compared to saline-treated ischemic mice ($44.43 \pm 5.94$ mm$^3$). Also when administrated 9 and 18 hours after ischemia, rabbit rhC1-INH was still effective, although to a minor extent ($23.63 \pm 4.11$ mm and $27.13 \pm 2.58$ mm$^3$ respectively). Twenty-four hours after ischemia the inhibitor lost its beneficial action ($41.92 \pm 2.76$ mm$^3$). (FIG. 3). In saline-treated mice, Fluoro-Jade staining showed that, neurodegeneration was present in striatum cortex and hippocampus. When administrated at early time points, rhC1-INH was able to counteract the neurodegeneration in hippocampus (up to 3 hours) and in cortex (up to 9 hours). When mice were treated with this inhibitor 6 and 9 hours after ischemia, some degenerating neurons were observed in hippocampus. At later time points of treatment (18 and 24 hours), when the ischemic volume was larger, Fluoro-Jade staining showed the presence of neurodegenerating neurons in cortex. At all time points considered, striatum showed an extensive neurodegeneration, both in saline- and rhC1-INH-treated animals (FIGS. 5, 6, 7). A semi-quantitative evaluation of Fluoro-Jade staining for each animal was performed by an investigator blinded to the experimental conditions (FIG. 4).

Dose-Response in Transient Ischemia

Figure 8:
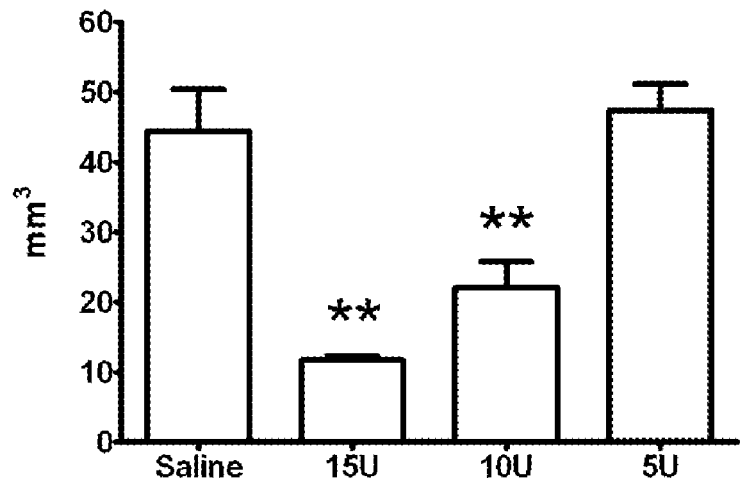
FIG. 8 Infarct volume assessed 48 h after ischemia in mice receiving saline or 5, 10, 15 U/mouse of rabbit rhC1-INH 3 hours after the onset of ischemia. Data are expressed as mean ±SEM (n=6 mice per group). **P<0.01 versus saline, one way ANOVA and Dunnett as post-hoc test.

Since the dose of C1-INH used in humans for hereditary angioedema is lower than the one we used in mice for stroke treatment, lower doses were used in our ischemic model. Based on the results of the previous experiment we chose 3 h post treatment for dose-response experiment. Different doses of rabbit rhC1-INH (5 and 10 units) were given 3 hours after the onset of ischemia and reperfusion. The dose of 10 U/mouse was still effective in reducing the ischemic volume ($22.10 \pm 3.65$ mm$^3$), while 5 U of rabbit rhC1-INH did not modify the extent of the brain damage ($47.39 \pm 4.08$ mm$^3$). These data show that rabbit rhC1-INH is able to modify the ischemic lesion in a dose-dependent manner (FIG. 8).

In mice treated with 10 U of rhC1-INH some neurodegenerating neurons, as evidenced by Fluoro-Jade staining, were observed in striatum but not in hippocampus and cortex, while 5 U-treated ischemic mice displayed a large neurodegeneration in striatum cortex (not shown).

General and focal neurological deficits did not show any significative variations either in time-window of efficacy or in dose-response experiment (not shown).

Comparison Between the Effect of pdC1-INH and rhC1-INH (from Rabbits and Cows)

Figure 9:
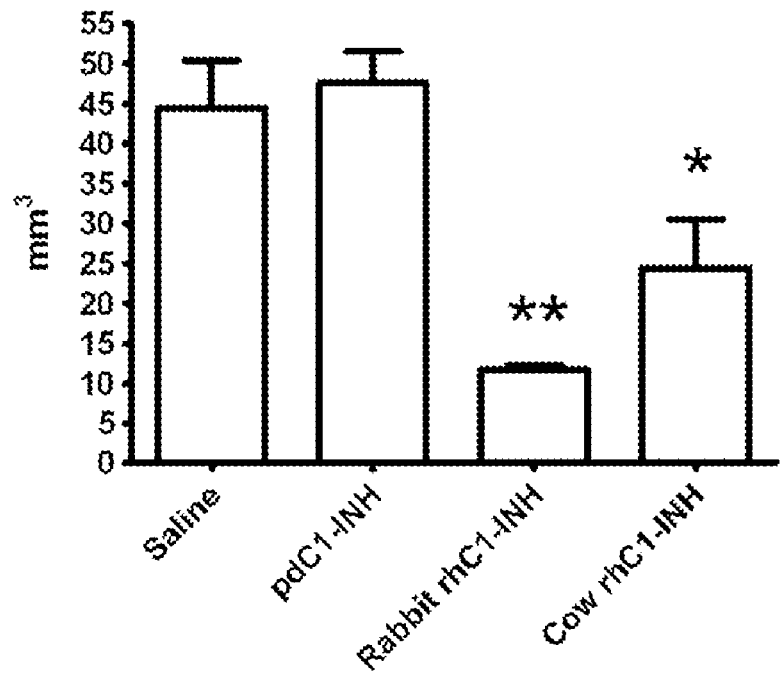
FIG. 9 Infarct volume assessed 48 h after ischemia in mice receiving saline or 15 U/mouse of pdC1-INH or cow, or rabbit rhC1-INH three hours after the onset of ischemia. Data are expressed as mean ±SEM (n=6 mice per group). *P<0.05, **P<0.01 versus saline, one way ANOVA and Dunnett as post-hoc test.
Figure 10A:
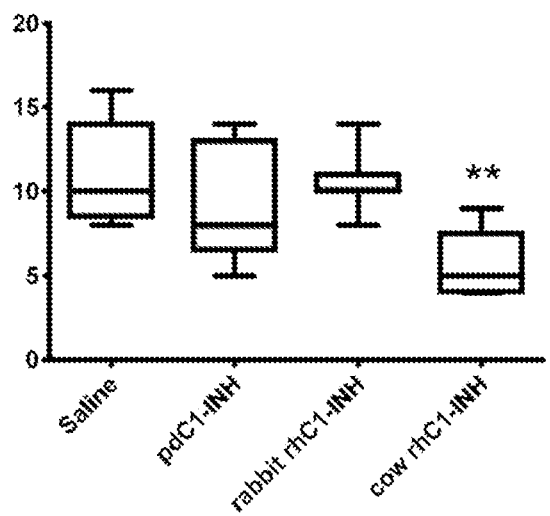
FIG. 10 General (upper panel 10a) and focal (lower panel 10b) deficits assessed 48 h after ischemia in mice receiving saline or 15 U/mouse of pdC1-INH or cow, or rabbit rhC1-INH three hours after the onset of ischemia. (n=6 mice per group). **P<0.01 versus saline, one way ANOVA and Kruskal-Wallis as post-hoc test.
Figure 10B:
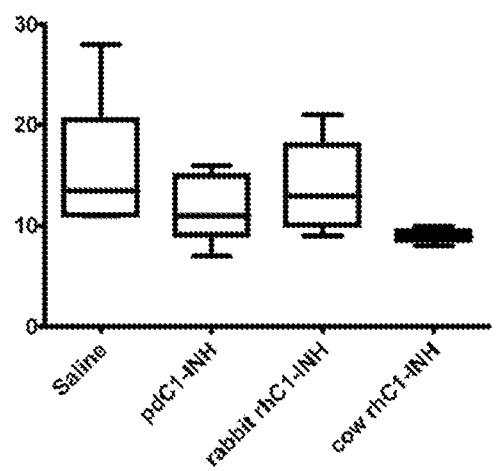
Figure 11:
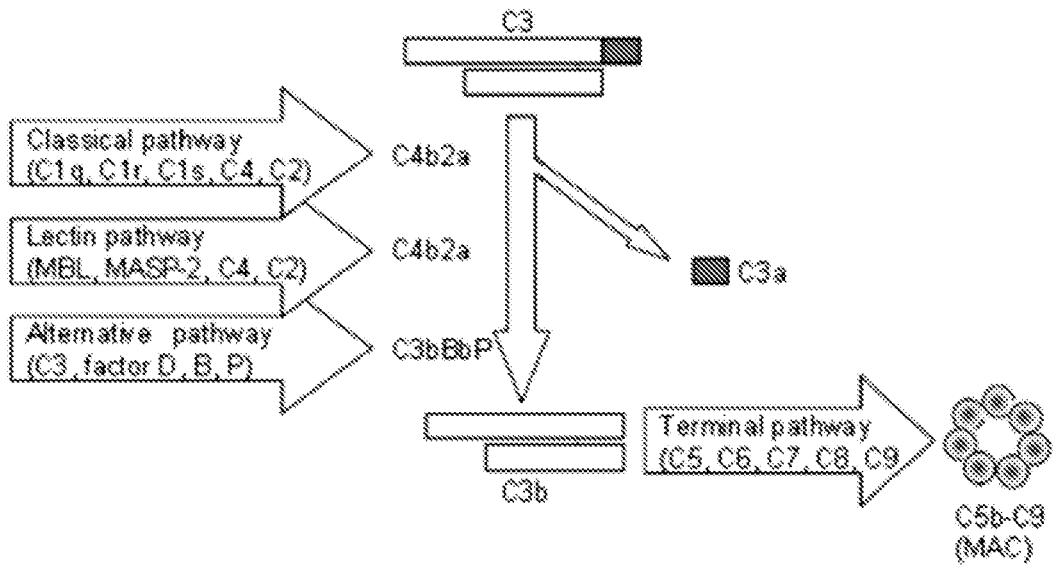
FIG. 11 Overview of the different pathways of complement activation.

Our previous data on pdC1-INH were obtained with a different model of transient cerebral ischemia. In order to directly compare pdC1-INH, cow rhC1-INH and rabbit rhC1-INH, these compounds were given to mice in which ischemia was induced with the same experimental protocol (silicone-coated filament). The inhibitors were administrated at the dose of 15 U/mouse 3 hours after the onset of ischemia. As expected, pdC1-INH was not able to exert a neuroprotective action at this time point ($47.39 \pm 4.08$ mm$^3$). At variance, cow rhC1-INH-treated ischemic mice showed a significantly reduced ischemic volume compared to saline-treated mice, even though to a lower extent than rabbit rhC1-INH-treated mice (FIG. 9). Surprisingly both general and focal deficits were significantly improved by cow rhC1-INH (FIG. 10).

Fluoro-Jade staining showed a large neurodegeneration in the brain of ischemic mice treated with pdC1-INH in all the 5 considered areas (cortex, striatum and hippocampus). The staining of the brain of cow rhC1-INH-treated mice showed a variable grade of neurodegeneration in cortex and hippocampus since in 3 out of 6 mice a marked neurodegeneration was observed in both these areas, while in the other 3 mice the neurodegeneration was present in a very little amount. The striatum displayed an extensive Fluoro-Jade staining in 6 out of 6 mice.

Comments

The most relevant data of this work is the time-window of efficacy of rabbit rhC1-INH. The dose of 15 U/mouse of rabbit rhC1-INH was able to significantly reduce the ischemic volume up to 18 hours after the onset of ischemia at variance with pdC1-INH that 3 hours after ischemia has already lost its neuroprotective effect. This surprising feature makes rhC1-INH a possible candidate for stroke therapy in humans. The different efficacy of pd and rhC1-INHs, could be due to the different glycosylation of the two molecules resulting in turn to a higher affinity for a mannose binding protein (MBP) of rhC1-INH as compared to the plasma derived one. Binding MBP, rhC1-INH causes the inhibition of the complement lectin pathway, involved in the pathogenesis of the damage in heart, kidney and gastrointestinal ischemia/reperfusion[7,9]. The role of this poorly characterized pathway is still unknown in brain ischemia and further experiments are required in order to clarify the mechanism of rhC1-INH neuroprotection.

The superior neuroprotective effect of rhC1INH over pdC1INH in the time-window after the onset of ischemia may further be explained by a more efficient targeting of the recombinant molecule to the site of tissue damage either through binding to cell-surface antigens and/or a more efficient tissue penetration. More research needs to be done to fully elucidate the exact molecular mechanism underlying the observation described in this invention.

Fluoro-Jade staining gives indirect evidence of how the lesion evolves in time. The early treatment with rhC1-INH provides a complete rescue of the ischemic penumbra (hippocampus and cortex). The later the treatment is administrated, the more neurons in the penumbra degenerate. These findings confirm that rhC1-INH exerts its neuroprotective action on ischemic penumbra. Rabbit rhC1-INH is able to reduce ischemic volume in a dose dependent-manner. The most effective dose of rhC1-INH (15 U/mouse, corresponding about to 600 U/kg), used for time-window of efficacy experiment, is much higher than the one used in humans for hereditary angioedema (about 25-100 U/kg). In order to verify if a lower dose was still effective in reducing neurodegeneration and ischemic infarct, a dose-response experiment was performed. The results showed that 400 U/kg (10 U/mouse) of rhC1-INH were still able to significantly counteract the ischemic insult, although to a lower extent. A dose 8 fold higher than the one used for HAE (5 U/mouse, 200 U/kg) was not effective. These findings are in line with evidence showing that large doses of C1-INH are required for therapeutic application in various inflammation settings[5]. In particular such doses are necessary to reach an important inhibitory effect on endothelial adhesion molecules[6], a mechanism involved in the pathogenesis of ischemia/reperfusion brain damage. Lastly, cow rhC1-INH provided neuroprotection, when given 3 hours after ischemia at the dose of 15 U/mouse, although less markedly than rabbit rhC1-INH.

The inhibitor from cow was also able to improve neurological deficits compared to saline-treated mice. These findings indicate that this molecule is able to ameliorate the general conditions of ischemic mice.

Example 3

Comparison of the Ability of RHC1INH and Plasma Derived C1INH to Inhibit Activation of the Classical and MBL Pathways Materials and Methods The effect of rhC1NH and pdC1INH (Cetor, Sanquin, Amsterdam, The Netherlands) on the function of the classical and lectin pathway was examined in the Wieslab TM complement system Screen (Euro-Diagnostica, Malmo, Sweeden) using two different sources of serum. One serum source is included in the kit, where it is used as a positive control (hereafter referred to as serum sample 1). The other serum sample was obtained from a commercially available pool of human serum (pool of 25 different donors; Kordia, Leiden, The Netherlands), hereafter referred to as serum sample 2. Both serum samples were incubated in independent triplo's with 0, 15, 30 and 75 μmol rhC1INH or pdC1INH for 30 min at room temperature. Therefore, stock solutions of pdC1INH and rhC1INH were diluted in water to appropriate concentrations. Volumes corresponding with 15, 30 and 75 μmol rhC1INH or pdC1INH were taken and adjusted to 15 μl with water. The buffer in which rhC1INH is dissolved (20 mM citrate, 0.19 M sucrose pH 6.8; 0.22 μm filtered) was taken along in the same dilutions as rhC1INH to control for interference with the Wieslab Complement System. The positive controls (PC) and negative controls (NC) from both the classical and MBL pathway (provided with the kit), and both serum samples were diluted 1/101 in Diluent CP for the classical pathway and Diluent MP for the MBL pathway according to manufacturer's instructions. Of these diluted sera, 127.5 μl was supplemented with 22.5 μl water, pdC1INH, rhC1INH or buffer and incubated for 30 minutes at RT. Next, 100 μl/well of PC, NC, Diluent CP or MP (blanks) and samples were pipetted on the appropriate plate and incubated for 1 hour at 37° C. After incubation the wells were washed 3 times with 300 μl/well washing solution and subsequently incubated for 30 minutes at room temperature with 100 μl/well of conjugate. After another wash, wells were incubated with 100 μl/well of substrate and again incubated for 30 minutes at room temperature. The reaction was stopped by the addition of 100 μl/well 5 mM EDTA and the absorbance was read at 405 nm.

For the calculation of the results, the absorbance of the blanks (Diluent CP or MP) was subtracted from the PC, NC and samples. The percentage complement activation was calculated per measurement with this formula: (Sample−NC)/(PC−NC)×100. This means that the PC is always set at 100%. For each condition the mean, standard deviation and CV % was calculated.

Results

Effect of rhC1INH and pd-C1INH on the Classical Pathway as Examined by Wielisa.

Figure 12:
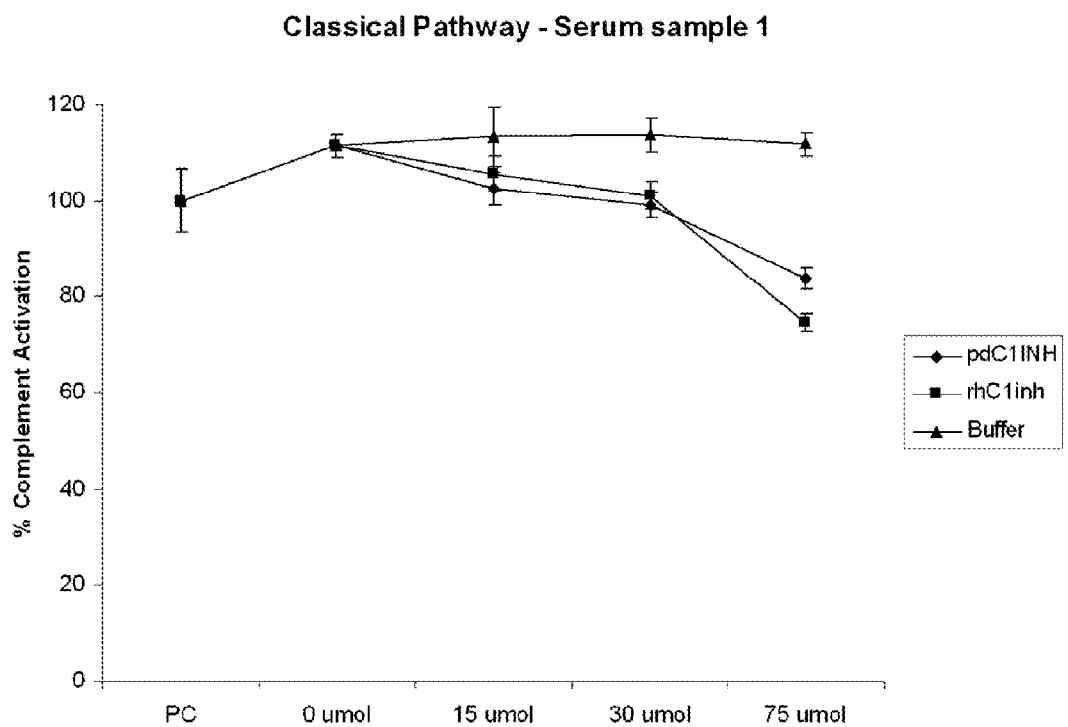
FIGS. 12, 13 Effect of rhC1INH and pdC1INH on activation of the classical complement pathway. Increasing doses of rhC1INH or pdC1INH (x-axis) was added to two different samples of normal human serum (sample 1 upper panel. sample 2 lower panel). As a control, the buffer in which rhC1INH is dissolved (20 mM citrate, 0.19 M sucrose pH 6.8; 0.22 µm filtered) was taken along in the same dilutions as rhC1INH. Readout was deposition of C5b-9, the normal serum control in the assay defining 100% (y-axis). Data are mean and SD (n=3).
Figure 13:
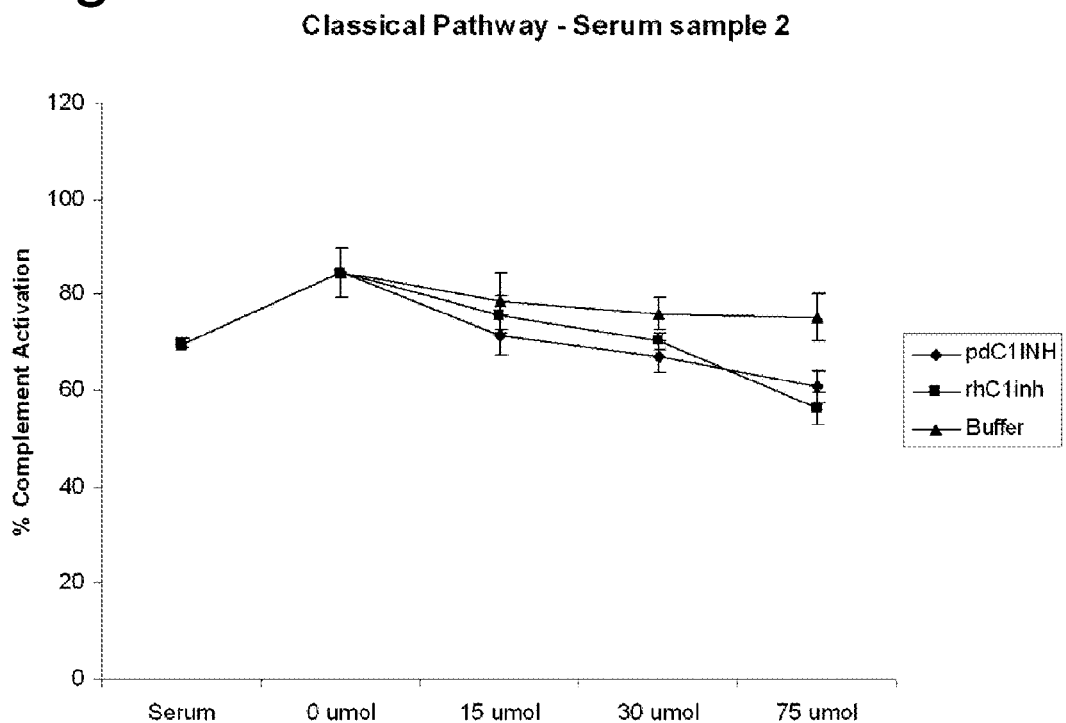

The inhibitory properties of both rhC1INH and pdC1INH on classical pathway activation were analyzed in two different serum samples. As shown in FIGS. 12, 13 and 16, both rhC1INH and pdC1INH dose-dependently reduced the classical pathway mediated C5b-9 deposition in both sera samples. Whereas rhC1INH—at a concentration of 75 μM—seems to inhibit the classical pathway activation in serum 1 slightly stronger than pdC1INH, such an effect was not seen in serum sample 2. At all other concentrations tested no differences in inhibitory properties were observed between rhC1INH and pdC1INH. Therefore, it was concluded that both rhC1INH and pdC1INH are equally effective in inhibiting classical pathway activation in human sera.

Effect of rhC1INH and pdC1INH on the MBL Pathway as Examined by Wielisa.

Figure 14:
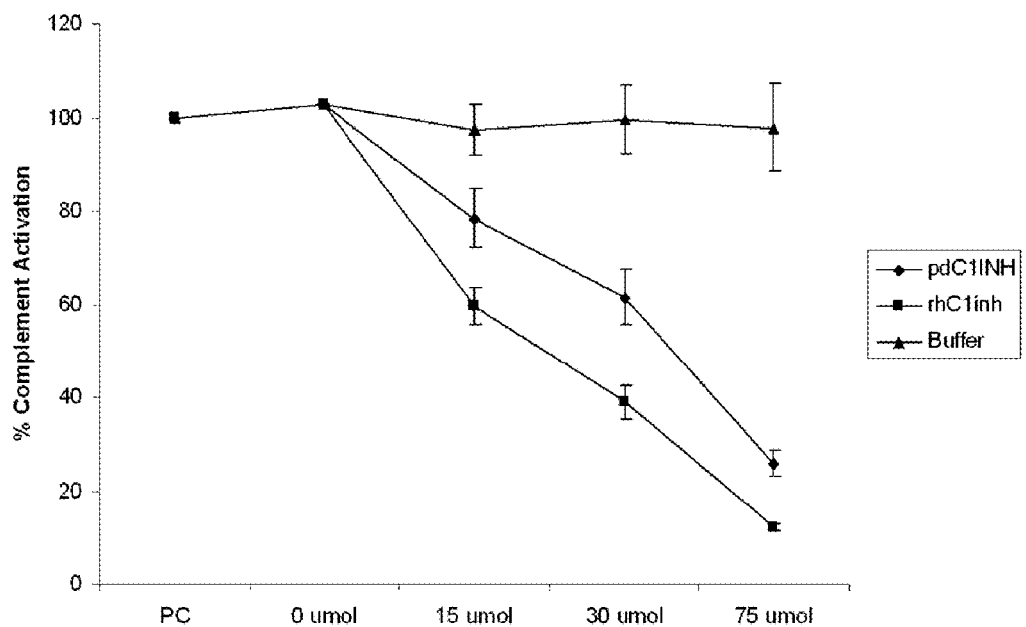
FIGS. 14, 15 Effect of rhc1INH and pdC1INH on activation of the MBL complement pathway. Increasing doses of rhC1INH or pdC1INH (x-axis) was added to two different samples of normal human serum serum (sample 1 upper panel. sample 2 lower panel). As a control, the buffer in which rhC1INH is dissolved (20 mM citrate, 0.19 M sucrose pH 6.8; 0.22 µm filtered) was taken along in the same dilutions as rhC1INH. Readout was deposition of C5b-9, the normal serum control in the assay defining 100% (y-axis). Data are mean and SD (n=3).
Figure 15:
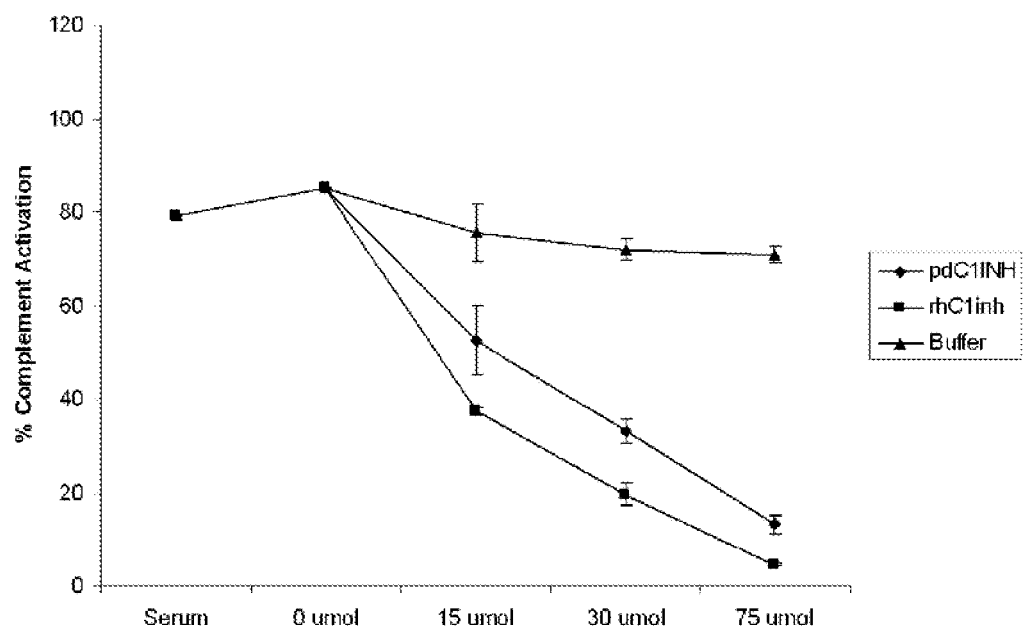

In the same set of experiments, also the inhibitory properties of both rhC1INH and pdC1INH on the MBL pathway activation were analyzed. As shown in FIGS. 14, 15 and 16, both rhC1INH and pdC1INH also dose-dependently reduced activation of the MBL pathway. However, in contrast to the classical pathway where no differences were seen, rhC1INH appeared to be a more potent inhibitor of the MBL pathway when compared to pdC1INH. At all 3 concentrations tested and in both serum samples, the rhC1INH-mediated inhibition of the MBL pathway is ~20% higher as compared to pdC1INH. Therefore, it was concluded that rhC1INH is a more effective inhibitor of the MBL pathway than pdC1INH.

Conclusion

The results show that both rhC1INH and pdC1INH are equally effective in inhibiting the classical pathway, but rhC1INH is a more potent inhibitor of the MBL pathway. At all concentrations tested, rhC1INH mediated MBL pathway inhibition was ~20% stronger as compared to pdC1INH.

REFERENCES

1. De Simoni, M. G. et al. Neuroprotection by complement (C1) inhibitor in mouse transient brain ischemia. *J Cereb Blood Flow Met* 23, 232-239 (2003).
2. De Simoni, M. G. et al. The powerful neuroprotective action of C1-inhibitor on brain ischemia-reperfusion injury does not require C1q. *Am J Pathol* 164, 1857-63 (2004).
3. Storini, C. et al. C1 inhibitor protects against brain ischemia-reperfusion injury via inhibition of cell recruitment and inflammation. *Neurobiol Disease* 19, 10-17 (2005).
4. Schmued, L. C. & Hopkins, K. J. Fluoro-Jade B: a high affinity fluorescent marker for the localization of neuronal degeneration. *Brain Res* 874, 123-30. (2000).
5. Caliezi, C. et al. C1 esterase inhibitor: an anti-inflammatory agent and its potential use in the treatment of diseases other than hereditary angioedema. *Pharmacol Rev* 52,91-112 (2000).
6. Cai, S. et al. A direct role for C1 inhibitor in regulation of leukocyte adhesion. *J Immunol* 174, 6462-6 (2005).
7. Walsh, M. C. et al. Mannose-binding lectin is a regulator of inflammation that accompanies myocardial ischemia and reperfusion injury. *J Immunol* 175, 541-6 (2005).
8. Moller-Kristensen, M. et al. Mannan-binding lectin recognizes structures on ischaemic reperfused mouse kidneys and is implicated in tissue injury. *Scand J Immunol* 61,426-34 (2005).
9. Hart, M. L. et al. Gastrointestinal ischemia-reperfusion injury is lectin complement pathway dependent without involving C1q. *J Immunol* 174, 6373-80 (2005).

The invention claimed is:

1. A method for preventing, reducing or treating ischemia and/or reperfusion injury, said method comprising administering to a subject in need thereof a pharmaceutical composition comprising a C 1 inhibitor recombinantly expressed in eukaryotic cell culture or in a transgenic nonhuman animal to have a reduced level of terminal sialic acid residues compared to plasma derived human C 1 inhibitor and a plasma half life shorter than 6 hours, wherein the administration of the C1 inhibitor occurs before 6 hours after the onset of ischemia or after reperfusion.

2. The method of claim 1, wherein the C1 inhibitor is administered at least one hour after the start of reperfusion.

3. The method of claim 1, wherein the C1 inhibitor comprises a glycan that has a terminal saccharide residue selected from galactose, N-acetylgalactosamine, N-acetylglucosamine, mannose and fucose.

4. The method of claim 1, wherein the C1 inhibitor is obtained from a transgenic nonhuman animal.

5. The method of claim 4, wherein the animal is a mammal and the C1 inhibitor is obtained from milk of the mammal.

6. The method of claim 4, wherein the transgenic nonhuman animal is a bovine or a lagomorph.

7. The method of claim 6, wherein the lagomorph is a rabbit.

8. The method of claim 1, wherein the C 1 inhibitor is administered at a dose range of 50 to 2000 units per kilogram body weight.

9. The method of claim 1, wherein the pharmaceutical composition is administered to said subject after, or in combination with, a thrombolytic agent.

10. The method of claim 1, wherein the pharmaceutical composition further comprises a thrombolytic agent.

11. The method of claim 1, wherein said administering of the pharmaceutical composition prevents, reduces or treats an unforeseen, sudden or acute incident of ischemia and/or reperfusion injury.

12. The method of claim 1, wherein said administering is after the subject has suffered a stroke.

13. The method of claim 12, wherein the C1 inhibitor exerts a neuroprotective effect.

14. The method of claim 13 wherein the neuroprotective effect of the C1 inhibitor is in hippocampus and/or cerebral cortex.

15. The method of claim 1, wherein said administering is after the subject has undergone an organ transplant.

16. The method of claim 1 wherein the subject is undergoing an organ transplant.

17. The method of claim 1, wherein the ischemia and/or reperfusion injury occurs in myocardium, kidney, gastrointestinal tract, or brain.

18. The method of claim 1, wherein the C1 inhibitor reduces size of a lesion resulting from the ischemia and/or reperfusion.

19. The method of claim 1, wherein the pharmaceutical composition is administered at least 30 minutes after the start of reperfusion.

20. The method of claim 1, wherein the pharmaceutical composition is administered 10 minutes after the start of reperfusion.

21. The method of claim 1, wherein the C1 inhibitor is administered at least 1 hour after onset of ischemia.

22. The method of claim 1, wherein the pharmaceutical composition is administered no more than 4 hours after onset of ischemia.

* * * * *

UNITED STATES PATENT AND TRADEMARK OFFICE
CERTIFICATE OF CORRECTION

PATENT NO. : 8,071,532 B2
APPLICATION NO. : 12/158987
DATED : December 6, 2011
INVENTOR(S) : Maurice Mannesse et al.

Page 1 of 1

It is certified that error appears in the above-identified patent and that said Letters Patent is hereby corrected as shown below:

Claim 1, Column 22, Line 1, delete "eukarvotic" and insert --eukaryotic--
Claim 3, Column 22, Line 11, delete the space between "N" and "-acetylgalactosamine"
Claim 8, Column 22, Line 21, delete the space between "C" and "1"

Signed and Sealed this
Thirteenth Day of March, 2012

David J. Kappos
*Director of the United States Patent and Trademark Office*